(12) United States Patent
Junghans et al.

(10) Patent No.: US 11,624,068 B2
(45) Date of Patent: Apr. 11, 2023

(54) COMPOSITIONS AND METHODS FOR IMPROVING IMMUNE SYSTEM FUNCTION

(71) Applicant: Tufts Medical Center, Inc., Boston, MA (US)

(72) Inventors: Richard P. Junghans, Boston, MA (US); Mumtaz Yaseen, Boston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 990 days.

(21) Appl. No.: 16/317,446

(22) PCT Filed: Jul. 14, 2017

(86) PCT No.: PCT/US2017/042147
§ 371 (c)(1),
(2) Date: Jan. 11, 2019

(87) PCT Pub. No.: WO2018/013929
PCT Pub. Date: Jan. 18, 2018

(65) Prior Publication Data
US 2019/0309301 A1    Oct. 10, 2019

Related U.S. Application Data

(60) Provisional application No. 62/362,825, filed on Jul. 15, 2016.

(51) Int. Cl.
| | | |
|---|---|---|
| *C12N 15/11* | (2006.01) | |
| *C12N 15/113* | (2010.01) | |
| *A61P 31/00* | (2006.01) | |
| *A61P 35/00* | (2006.01) | |
| *A61K 31/4439* | (2006.01) | |
| *A61K 31/444* | (2006.01) | |
| *A61K 31/496* | (2006.01) | |
| *A61K 31/5377* | (2006.01) | |
| *A61K 31/706* | (2006.01) | |
| *A61K 31/713* | (2006.01) | |
| *A61K 35/17* | (2015.01) | |
| *C12N 9/10* | (2006.01) | |
| *A61P 37/04* | (2006.01) | |
| *A61K 31/7088* | (2006.01) | |
| *A61K 31/7105* | (2006.01) | |
| *C07K 14/47* | (2006.01) | |
| *A61K 45/06* | (2006.01) | |

(52) U.S. Cl.
CPC ........ *C12N 15/1137* (2013.01); *A61K 31/444* (2013.01); *A61K 31/4439* (2013.01); *A61K 31/496* (2013.01); *A61K 31/5377* (2013.01); *A61K 31/706* (2013.01); *A61K 31/7088* (2013.01); *A61K 31/713* (2013.01); *A61K 31/7105* (2013.01); *A61K 35/17* (2013.01); *A61K 45/06* (2013.01); *A61P 31/00* (2018.01); *A61P 35/00* (2018.01); *A61P 37/04* (2018.01); *C07K 14/4702* (2013.01); *C12N 9/1007* (2013.01); *C12Y 201/01043* (2013.01); *C12N 2310/14* (2013.01)

(58) Field of Classification Search
CPC .................................................. C12N 15/1137
See application file for complete search history.

(56) References Cited

U.S. PATENT DOCUMENTS

2008/0311039 A1* 12/2008 Bonavida ......... G01N 33/57426
424/9.1

FOREIGN PATENT DOCUMENTS

| WO | WO-2007/011372 A2 | 1/2007 |
| WO | WO-2015/120372 A2 | 8/2015 |
| WO | WO-2015/128837 A1 | 9/2015 |

OTHER PUBLICATIONS

Zhao et al. ("Cancer mediates effector T cell dysfunction by targeting microRNAs and EZH2 via 64—glycolysis restriction," Nat Immunol, Nov. 2, 2015 (Nov. 2, 2015), vol. 17, No. 1, pp. 95-103) (Year: 2015).*
Peng et al. ("Epigenetic silencing of TH 1-type chemokines shapes tumour immunity and immunotherapy," Nature, Oct. 26, 2015 (Oct. 26, 2015), vol. 527, No. 7577, pp. 249-253). (Year: 2015).*
Zhao et al. ("Cancer mediates effector T cell dysfunction by targeting microRNAs and EZH2 via glycolysis restriction," Nat Immunol , Nov. 2, 2015 (Nov. 2, 2015), vol. 17, No. 1, pp. 95-103). (Year: 2015).*
Barbee et al. (Annals of Pharmacotherapy 2015, vol. 49(8) 907-937). (Year: 2015).*
White et al. (American Society for Microbiology. Clinical Microbiology Reviews. vol. 27, Issue 3, Jul. 2014, pp. 463-481). (Year: 2014).*
Chen et al., "Enhancer of zeste homolog 2 is a negative regulator of mitochondria-mediated innate immune responses," with Supplementary Information, J. Immunol. 191(5):2614-2623 (2013) (14 pages).
Chen et al., "Yin Yang 1 promotes thymocyte survival by downregulating p53," J. Immunol. 196(6):2572-2582 (2016).
International Preliminary Report on Patentability dated Jan. 24, 2019, for PCT International Application No. PCT/US2017/042147, Junghans et al., "Compositions and Methods for Improving Immune System Function," filed Jul. 14, 2017 (10 pages).

(Continued)

Primary Examiner — Scott Long
(74) Attorney, Agent, or Firm — Clark & Elbing LLP; Susan M. Michaud

(57) ABSTRACT

Provided herein are compositions and methods for improving immune system function. In particular, provided herein are compositions, methods, and uses of YY1 and EZH2 inhibitors for preventing and reversing T-cell exhaustion (e.g., for use in immunotherapy).

22 Claims, 19 Drawing Sheets
Specification includes a Sequence Listing.

(56) References Cited

OTHER PUBLICATIONS

International Search Report and Written Opinion dated Oct. 3, 2017, for PCT International Application No. PCT/US2017/042147, Junghans et al., "Compositions and Methods for Improving Immune System Function," filed Jul. 14, 2017 (12 pages).
Kim et al., "In vivo YY1 knockdown effects on genomic imprinting," Hum. Mol. Genet. 17(3):391-401 (2008).
Partial Supplementary European Search Report dated Jul. 9, 2020 for European Application No. 17828534.2, Junghans et al., "Compositions and Methods for Improving Immune System Function," filed Jul. 14, 2020 (15 pages).
Peng et al., "Epigenetic silencing of TH1-type chemokines shapes tumour immunity and immunotherapy," Nature 527(7577):249-253 (2015) (17 pages).
Sasaki et al., "Overexpression of Enhancer of zeste homolog 2 with trimethylation of lysine 27 on histone H3 in adult T-cell leukemia/lymphoma as a target for epigenetic therapy," Haematologica 96(5):712-719(2011).
Zhao et al., "Cancer mediates effector T cell dysfunction by targeting microRNAs and EZH2 via glycolysis restriction," Nat. Immunol. 17(1):95-103 (2015) (11 pages).
Banerjee et al., "YY1 is required for germinal center B cell development," PLoS One 11(5):e0155311 (2016) (11 pages).
Extended European Search Report dated Nov. 18, 2020 for European Patent Application No. 17828534.2, Junghans et al., "Compositions and Methods for Improving Immune System Function," filed Jul. 14, 2017 (14 pages).
Golubovskaya et al., "Different subsets of T cells, memory, effector functions, and CAR-T immunotherapy," Cancers 8(3):36 (2016) (12 pages).
Till et al., "Adoptive immunotherapy for indolent non-Hodgkin lymphoma and mantle cell lymphoma using genetically modified autologous CD20-specific T cells," Blood 112(6):2261-2271 (2008).
Tumes et al., "The polycomb protein Ezh2 regulates differentiation and plasticity of CD4+ T helper type 1 and type 2 cells," Immunity 39(5):819-832 (2013).
Blank et al., "Defining 'T cell exhaustion'," Nat Rev Immunol. 19(11):655-74 (Sep. 30, 2019) (39 pages).
Miggelbrink et al., "CD4 T-Cell Exhaustion: Does It Exist and What Are Its Roles in Cancer" Clin Cancer Res. 27(21):5742-52 (Nov. 2021).

* cited by examiner

Figure 13

CCTTGAATGCAAACCTTTTCTGAGTATTAACAAATCGTACCTTAAAAAATGTACAATGACATTAA (SEQ ID No. 2)
GAGACTTAAACAGATATAATCATTTAAATAAACAGTAAATAGCGTAAAACAGTAACTCAAGCTCAATAAGC
ATTTAAGTATTCTAAGTCTAGTATTCCTAGTCTGACATGTAACAGAAGCAATCTATCTATGCAAT
TAGCTCATTGTGTGTGGATAAAAAGGTAAACCATTCGAAACACTTCGAAACAATACTTCCTGTTTAT
CACAAAATCTAACACTTAATTCTTTCATCGTTACTCGTCTGTCCACACAATATGCTAATCACA
TGTTCAGTGTAGTTTATGACAAAGAAATTTCGAGTACTTTGTATCCCACCCCCTTAAGAAA
GGAAGGAAAAACTGTTTCATACAGAAGGCGTTAATTGCAT GAATTAGAGCTATCAC CTAGTGTGGC
　　　　　　NF-AT 1/2/3　　AP1　　　　　　　　AP2　　　AP3
CTAATGTAACAAAGAGGGATTCACCTACACCATTCAGTCTTGGGGGTTAAAGAAATTCC
　　　　　　　NF-κB　　　　　　　　　　　　　　　　CD28RE
AAGAGTCATCAGCAAGGGAAAAATGAAGGTAATGTTTTCAGAGTAAAGTCTTTGAAAATA
TGTGTAATATGTAAACATTTGACACCCCATAAATATTTTTCAGAATAACAGTATAAATGCATCT
　　OCT-1　　　　　　　　　　Yin-Yang1　HMG1　　　　TFIID
CTTGTTCAAGAGTTCCCTATCACTCTTTAATCACTACTCACAGTAACCTCAACTCTGCCACAATG
ACAGGAATGCAACTCCGTCTTGCACTAACAGTCTTGCACTAACAGTGCCACTTACTTCA
AGTTCTACAAGAAAACACAGCCTACAACGCATTACCTCCTGGAGCATTTACCAGAYGATTTCAAATG
GAATTAATGTAAGTAAATATTCCTTCTAACATTAGTAACATTACTAGCTGGAAATCATTCT
TAATAACAATG

PD1 Promoter — YY1 site

| Matrix | Factor name | Position (strand) | Core score | Matrix score | Sequence | |
|---|---|---|---|---|---|---|
| V$YY1_Q4_01 | YY1 | 207 (+) | 1.000 | 0.989 | ccgtaaAATGGgggc | (SEQ ID No. 3) |
| V$YY1_Q6_03 | YY1 | 211 (-) | 1.000 | 1.000 | aaAATGG | (SEQ ID No. 4) |
| V$MAF_Q6_01 | MAF | 254 (+) | 1.000 | 0.964 | tgcggAGTCAt | (SEQ ID No. 5) |
| V$MAF_Q4 | MAF | 255 (+) | 1.000 | 0.968 | gcggAGTCAt | (SEQ ID No. 6) |
| V$CJUN_Q6 | C-Jun | 258 (-) | 1.000 | 1.000 | gAGTCA | (SEQ ID No. 7) |
| V$STAT3_01 | STAT3 | 291 (-) | 0.908 | 0.824 | tggcaggtccgGGAAGtggag | (SEQ ID No. 8) |

B)

LAG3 Promoter — YY1 site

| Matrix | Factor name | Position (strand) | Core score | Matrix score | Sequence | |
|---|---|---|---|---|---|---|
| V$NFAT1_Q4 | NF-AT1 | 23 (+) | 1.000 | 1.000 | GGAAAa | (SEQ ID No. 9) |
| V$BLIMP1_03 | Blimp-1 | 61 (-) | 1.000 | 0.873 | tgTCCAAtacag | (SEQ ID No. 10) |
| V$XBP1_01 | XBP-1 | 74 (-) | 1.000 | 0.883 | gcttagCACGTaatgaa | (SEQ ID No. 11) |
| V$OCT1_03 | Oct-1 | 80 (+) | 1.000 | 0.994 | cacGTAATgaagc | (SEQ ID No. 12) |
| V$TCF1_Q5 | TCF-1 | 124 (-) | 1.000 | 1.000 | aCAAAG | (SEQ ID No. 13) |
| V$YY1_Q6_03 | YY1 | 154 (+) | 1.000 | 1.000 | CCATTt | (SEQ ID No. 14) |
| V$ETS_B | c-Ets | 172 (-) | 1.000 | 0.935 | taaggcTTCCTgtc | (SEQ ID No. 15) |

C)

TIM3 Promoter — GATA3 site

| Matrix | Factor name | Position (strand) | Core score | Matrix score | Sequence | |
|---|---|---|---|---|---|---|
| V$GATA3_Q4 | GATA-3 | 12 (-) | 1.000 | 1.000 | tTATCT | (SEQ ID No. 16) |
| V$HMGIY_Q3 | HMGIY | 18 (+) | 1.000 | 0.939 | aatacAATTTtctca | (SEQ ID No. 17) |
| V$CEBPG_Q6 | C/EBPgamma | 29 (+) | 0.845 | 0.904 | ctcATTTTataaa | (SEQ ID No. 18) |
| V$POU6F1_01 | POU6F1 | 37 (-) | 1.000 | 0.894 | ATAAAttatat | (SEQ ID No. 19) |
| V$CETS1_Q6 | C-ets-1 | 190 (-) | 1.000 | 1.000 | acTTCCt | (SEQ ID No. 20) |
| V$SPI1_04 | SPI1 | 190 (-) | 1.000 | 1.000 | acTTCCT | (SEQ ID No. 21) |
| V$ELF1_Q5 | Elf-1 | 191 (-) | 1.000 | 1.000 | cTTCCT | (SEQ ID No. 22) |
| V$SPI1_Q5 | SPI1 | 191 (-) | 1.000 | 1.000 | cTTCCT | (SEQ ID No. 23) |

D)

YY1 Promoter — cJun/ATF2

| Matrix | Factor name | Position (strand) | Core score | Matrix score | Sequence | |
|---|---|---|---|---|---|---|
| V$PAX4_01 | Pax-4 | 310 (-) | 0.881 | 0.843 | ccgcccacccgCCTCAacccc | (SEQ ID No. 24) |
| V$CREBP1_Q2 | CRE-BP1 | 555 (+) | 1.000 | 0.972 | gcTGACGtcacg | (SEQ ID No. 25) |
| V$CREB_01 | CREB | 557 (+) | 1.000 | 1.000 | TGACGtca | (SEQ ID No. 26) |
| V$CREB_01 | CREB | 557 (-) | 1.000 | 1.000 | tgaCGTCA | (SEQ ID No. 27) |
| V$CREBP1CJUN_01 | CRE-BP1/c-Jun | 557 (+) | 1.000 | 1.000 | tGACGTca | (SEQ ID No. 28) |
| V$CREBP1CJUN_01 | CRE-BP1/c-Jun | 557 (-) | 1.000 | 1.000 | tgACGTCa | (SEQ ID No. 29) |
| V$PAX4_01 | Pax-4 | 557 (+) | 0.977 | 0.897 | tgacgTCACGcgccgcgggcc | (SEQ ID No. 30) |
| V$CDPCR1_01 | CDP CR1 | 672 (-) | 1.000 | 0.930 | cagaTCGATt | (SEQ ID No. 31) |

E)

| Gene | Transcription Factor | Position from TSS |
|---|---|---|
| IL2 | YY1 | -5 |
| IFNγ | YY1/AP1 | -198/-189 |
| PD1 | YY1 | -433 |
| LAG3 | YY1 | -492 |
| TIM3 | GATA3/YY1 | -633 |
| YY1 | cJun/ATF2 | -136 |
| Ezh2 | cJun | -4 |

```
                       SEQUENCE LISTING

<160> NUMBER OF SEQ ID NOS: 53

<210> SEQ ID NO 1
<211> LENGTH: 49
<212> TYPE: DNA
<213> ORGANISM: Homo sapiens

<400> SEQUENCE: 1
gcgcgtgacg tcacgcgccg cgggccagcc agggcgcgtg cgagccgcc            49

<210> SEQ ID NO 2
<211> LENGTH: 968
<212> TYPE: DNA
<213> ORGANISM: Homo sapiens

<400> SEQUENCE: 2
ccttgaatgc aaacctttt ctgagtattt aacaatcgca ccctttaaaa aatgtacaat      60
agacattaag agacttaaac agatatataa tcattttaaa ttaaaatagc gttaaacagt     120
acctcaagct caataagcat tttaagtatt ctaatcttag tatttctcta gctgacatgt     180
aagaagcaat ctatcttatt gtatgcaatt agctcattgt gtggataaaa aggtaaaacc     240
attctgaaac aggaaaccaa tacacttcct gttttatcaa caaatctaaa catttattct     300
tttcatctgt ttactcttgc tcttgtccac cacaatatgc tattcacatg ttcagtgtag     360
ttttatgaca aagaaaattt tctgagttac ttttgtatcc ccacccctt aaagaaagag      420 gaaaactgtt tcatacagaa ggcgttaatt gcatgaatta gagctatcac ctaagtgtgg    480
cctaatgtaa caaagaggga tttcacctac atccattcag tcagtctttg gggtttaaag    540
aaattccaaa gagtcatcag aagaggaaaa atgaaggtaa tgttttttca gacaggtaaa    600
gtctttgaaa atatgtgtaa tatgtaaaac attttgacac ccccataata ttttccaga     660 attaacagta taaattgcat ctcttgttca agagttccct atcactctct ttaatcacta    720
ctcacagtaa cctcaactcc tgccacaatg tacaggatgc aactcctgtc ttgcattgca    780
ctaagtcttg cacttgtcac aaacagtgca cctacttcaa gttctacaaa gaaaacacag    840
ctacaactgg agcatttact gctggattta cagatgattt tgaatggaat taatgtaagt    900
atatttcctt tcttactaaa attattacat ttagtaatct agctggagat catttcttaa    960
taacaatg                                                             968

<210> SEQ ID NO 3
```

```
<211> LENGTH: 15
<212> TYPE: DNA
<213> ORGANISM: Homo sapiens

<400> SEQUENCE: 3
ccgtaaaatg ggggc                                              15

<210> SEQ ID NO 4
<211> LENGTH: 7
<212> TYPE: DNA
<213> ORGANISM: Homo sapiens

<400> SEQUENCE: 4 aaaatgg                                                        7

<210> SEQ ID NO 5
<211> LENGTH: 11
<212> TYPE: DNA
<213> ORGANISM: Homo sapiens

<400> SEQUENCE: 5
tgcggagtca t                                                  11

<210> SEQ ID NO 6
<211> LENGTH: 10
<212> TYPE: DNA
<213> ORGANISM: Homo sapiens

<400> SEQUENCE: 6
gcggagtcat                                                    10

<210> SEQ ID NO 7
<211> LENGTH: 6
<212> TYPE: DNA
<213> ORGANISM: Homo sapiens

<400> SEQUENCE: 7 gagtca                                                         6

<210> SEQ ID NO 8
<211> LENGTH: 21
<212> TYPE: DNA
<213> ORGANISM: Homo sapiens

<400> SEQUENCE: 8
tggcaggtcc gggaagtgga g                                       21

<210> SEQ ID NO 9
<211> LENGTH: 6
<212> TYPE: DNA
<213> ORGANISM: Homo sapiens

<400> SEQUENCE: 9 ggaaaa                                                         6

<210> SEQ ID NO 10
<211> LENGTH: 12
<212> TYPE: DNA
<213> ORGANISM: Homo sapiens

<400> SEQUENCE: 10
tgtccaatac ag                                                 12
```

-continued

```
<210> SEQ ID NO 11
<211> LENGTH: 17
<212> TYPE: DNA
<213> ORGANISM: Homo sapiens

<400> SEQUENCE: 11
gcttagcacg taatgaa                                                    17

<210> SEQ ID NO 12
<211> LENGTH: 13
<212> TYPE: DNA
<213> ORGANISM: Homo sapiens

<400> SEQUENCE: 12
cacgtaatga agc                                                        13

<210> SEQ ID NO 13
<211> LENGTH: 6
<212> TYPE: DNA
<213> ORGANISM: Homo sapiens

<400> SEQUENCE: 13 acaaag                                                                 6

<210> SEQ ID NO 14
<211> LENGTH: 7
<212> TYPE: DNA
<213> ORGANISM: Homo sapiens

<400> SEQUENCE: 14 ccatttt                                                                7

<210> SEQ ID NO 15
<211> LENGTH: 14
<212> TYPE: DNA
<213> ORGANISM: Homo sapiens

<400> SEQUENCE: 15
taaggcttcc tgtc                                                       14

<210> SEQ ID NO 16
<211> LENGTH: 6
<212> TYPE: DNA
<213> ORGANISM: Homo sapiens

<400> SEQUENCE: 16 ttatct                                                                 6

<210> SEQ ID NO 17
<211> LENGTH: 15
<212> TYPE: DNA
<213> ORGANISM: Homo sapiens

<400> SEQUENCE: 17
aatacaattt tctca                                                      15

<210> SEQ ID NO 18
<211> LENGTH: 13
<212> TYPE: DNA
<213> ORGANISM: Homo sapiens

<400> SEQUENCE: 18
ctcattttat aaa                                                        13
```

```
<210> SEQ ID NO 19
<211> LENGTH: 11
<212> TYPE: DNA
<213> ORGANISM: Homo sapiens

<400> SEQUENCE: 19
ataaattata t                                                          11

<210> SEQ ID NO 20
<211> LENGTH: 7
<212> TYPE: DNA
<213> ORGANISM: Homo sapiens

<400> SEQUENCE: 20 acttcct                                                                7

<210> SEQ ID NO 21
<211> LENGTH: 7
<212> TYPE: DNA
<213> ORGANISM: Homo sapiens

<400> SEQUENCE: 21 acttcct                                                                7

<210> SEQ ID NO 22
<211> LENGTH: 6
<212> TYPE: DNA
<213> ORGANISM: Homo sapiens

<400> SEQUENCE: 22 cttcct                                                                 6

<210> SEQ ID NO 23
<211> LENGTH: 6
<212> TYPE: DNA
<213> ORGANISM: Homo sapiens

<400> SEQUENCE: 23 cttcct                                                                 6

<210> SEQ ID NO 24
<211> LENGTH: 21
<212> TYPE: DNA
<213> ORGANISM: Homo sapiens

<400> SEQUENCE: 24
ccgcccaccc gcctcaaccc c                                               21

<210> SEQ ID NO 25
<211> LENGTH: 12
<212> TYPE: DNA
<213> ORGANISM: Homo sapiens

<400> SEQUENCE: 25
gctgacgtca cg                                                         12

<210> SEQ ID NO 26
<211> LENGTH: 8
<212> TYPE: DNA
<213> ORGANISM: Homo sapiens

<400> SEQUENCE: 26 tgacgtca                                                               8
```

```
<210> SEQ ID NO 27
<211> LENGTH: 8
<212> TYPE: DNA
<213> ORGANISM: Homo sapiens

<400> SEQUENCE: 27 tgacgtca                                                                    8

<210> SEQ ID NO 28
<211> LENGTH: 8
<212> TYPE: DNA
<213> ORGANISM: Homo sapiens

<400> SEQUENCE: 28 tgacgtca                                                                    8

<210> SEQ ID NO 29
<211> LENGTH: 8
<212> TYPE: DNA
<213> ORGANISM: Homo sapiens

<400> SEQUENCE: 29 tgacgtca                                                                    8

<210> SEQ ID NO 30
<211> LENGTH: 21
<212> TYPE: DNA
<213> ORGANISM: Homo sapiens

<400> SEQUENCE: 30
tgacgtcacg cgccgcgggc c                                                    21

<210> SEQ ID NO 31
<211> LENGTH: 10
<212> TYPE: DNA
<213> ORGANISM: Homo sapiens

<400> SEQUENCE: 31
cagatcgatt                                                                 10

<210> SEQ ID NO 32
<211> LENGTH: 15
<212> TYPE: DNA
<213> ORGANISM: Homo sapiens

<400> SEQUENCE: 32
aatgggtctg tctca                                                           15

<210> SEQ ID NO 33
<211> LENGTH: 12
<212> TYPE: DNA
<213> ORGANISM: Homo sapiens

<400> SEQUENCE: 33
cccataatat tt                                                              12

<210> SEQ ID NO 34
<211> LENGTH: 6
<212> TYPE: DNA
<213> ORGANISM: Homo sapiens

<400> SEQUENCE: 34
``` agataa                                                                          6

<210> SEQ ID NO 35
<211> LENGTH: 8
<212> TYPE: DNA
<213> ORGANISM: Homo sapiens

<400> SEQUENCE: 35 aaatgggg                                                                        8

<210> SEQ ID NO 36
<211> LENGTH: 8
<212> TYPE: DNA
<213> ORGANISM: Homo sapiens

<400> SEQUENCE: 36 accatttt                                                                        8

<210> SEQ ID NO 37
<211> LENGTH: 10
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a, c, g, or t

<400> SEQUENCE: 37 ccgccatntt                                                                     10

<210> SEQ ID NO 38
<211> LENGTH: 10
<212> TYPE: DNA
<213> ORGANISM: Homo sapiens

<400> SEQUENCE: 38
cccccataat                                                                     10

<210> SEQ ID NO 39
<211> LENGTH: 10
<212> TYPE: DNA
<213> ORGANISM: Homo sapiens

<400> SEQUENCE: 39
aacaaagaac                                                                     10

<210> SEQ ID NO 40
<211> LENGTH: 8
<212> TYPE: DNA
<213> ORGANISM: Homo sapiens

<400> SEQUENCE: 40 tgacgtca                                                                        8

<210> SEQ ID NO 41
<211> LENGTH: 8
<212> TYPE: DNA
<213> ORGANISM: Homo sapiens

<400> SEQUENCE: 41 cggcataa                                                                        8

<210> SEQ ID NO 42
<211> LENGTH: 24

```
<212> TYPE: DNA
<213> ORGANISM: Homo sapiens

<400> SEQUENCE: 42
catcagaaga ggaaaaatga aggt                                              24

<210> SEQ ID NO 43
<211> LENGTH: 24
<212> TYPE: DNA
<213> ORGANISM: Homo sapiens

<400> SEQUENCE: 43
tcttgaacaa gagatgcaat ttat                                              24

<210> SEQ ID NO 44
<211> LENGTH: 37
<212> TYPE: DNA
<213> ORGANISM: Homo sapiens

<400> SEQUENCE: 44
ggcggtggcg gcggcggcgg cgcgctgacg tcacgcg                                37

<210> SEQ ID NO 45
<211> LENGTH: 18
<212> TYPE: DNA
<213> ORGANISM: Homo sapiens

<400> SEQUENCE: 45
cgcgcgactg cagtgcgc                                                     18

<210> SEQ ID NO 46
<211> LENGTH: 21
<212> TYPE: DNA
<213> ORGANISM: Artificial sequence
<220> FEATURE:
<223> OTHER INFORMATION: Synthetic primer

<400> SEQUENCE: 46
aactcctgtc ttgcattgca c                                                 21

<210> SEQ ID NO 47
<211> LENGTH: 21
<212> TYPE: DNA
<213> ORGANISM: Artificial sequence
<220> FEATURE:
<223> OTHER INFORMATION: Synthetic primer

<400> SEQUENCE: 47
gctccagttg tagctgtgtt t                                                 21

<210> SEQ ID NO 48
<211> LENGTH: 23
<212> TYPE: DNA
<213> ORGANISM: Artificial sequence
<220> FEATURE:
<223> OTHER INFORMATION: Synthetic primer

<400> SEQUENCE: 48
tcggtaactg acttgaatgt cca                                               23

<210> SEQ ID NO 49
<211> LENGTH: 21
<212> TYPE: DNA
<213> ORGANISM: Artificial sequence
<220> FEATURE:
```

```
<223> OTHER INFORMATION: Synthetic primer

<400> SEQUENCE: 49
tcgcttccct gttttagctg c                                             21

<210> SEQ ID NO 50
<211> LENGTH: 21
<212> TYPE: DNA
<213> ORGANISM: Artificial sequence
<220> FEATURE:
<223> OTHER INFORMATION: Synthetic primer

<400> SEQUENCE: 50
acggcttcga ggatcagatt c                                             21

<210> SEQ ID NO 51
<211> LENGTH: 21
<212> TYPE: DNA
<213> ORGANISM: Artificial sequence
<220> FEATURE:
<223> OTHER INFORMATION: Synthetic primer

<400> SEQUENCE: 51
tgaccagcgt ttgttcaatg t                                             21

<210> SEQ ID NO 52
<211> LENGTH: 22
<212> TYPE: DNA
<213> ORGANISM: Artificial sequence
<220> FEATURE:
<223> OTHER INFORMATION: Synthetic primer

<400> SEQUENCE: 52
acaactttgg tatcgtggaa gg                                            22

<210> SEQ ID NO 53
<211> LENGTH: 19
<212> TYPE: DNA
<213> ORGANISM: Artificial sequence
<220> FEATURE:
<223> OTHER INFORMATION: Synthetic primer

<400> SEQUENCE: 53
gccatcacgc cacagtttc                                                19
```

COMPOSITIONS AND METHODS FOR IMPROVING IMMUNE SYSTEM FUNCTION

CROSS REFERENCE TO RELATED APPLICATION

This application is a U.S. 371 national phase entry of International Patent Application No. PCT/US2017/042147, filed Jul. 14, 2017, which claims priority to U.S. Provisional Patent Application Ser. No. 62/362,825, filed Jul. 15, 2016, which are herein incorporated by reference in their entireties.

STATEMENT REGARDING FEDERALLY SPONSORED RESEARCH OR DEVELOPMENT

This invention was made with government support under grants AI102847 and AI110158 awarded by the National Institutes of Health and grant W81XWH-21-1-0185 awarded by the United States Army. The government has certain rights in the invention.

FIELD

Provided herein are compositions and methods for improving immune system function. In particular, provided herein are compositions, methods, and uses of YY1 and EZH2 inhibitors for preventing and reversing T-cell exhaustion (e.g., for use in immunotherapy).

BACKGROUND

T cells of patients affected by malignancy or chronic infections become exhausted (Zajac et al., 1998 J Exp Med 188, 2205-2213). Tumor antigen-reactive T cells are particularly vulnerable to exhaustion upon entering into an antigen-rich environment where they are likely to be stimulated persistently (Balkhi et al., 2015 Cytokine 71, 339-347; Yi et al., 2010 Immunology 129, 474-481). Exhausted T cells have low proliferative capacity, express inhibitory receptor molecules such as programmed death 1 (PD1), T-cell immunoglobulin and mucin domain-containing protein 3 (TIM3), lymphocyte-activation gene 3 (LAG3). Concurrently, T cells lose the ability to produce type I cytokines (Balkhi et al., 2015, supra; Virgin et al., 2009 Cell 138, 30-50; Wherry, 2011 Nat Immunol 12, 492-499), of which IL2 may be one of the most important. IL2 cytokine plays a pivotal role in clonal expansion of tumor-reactive T cells, in the survival of these cells, and their persistence at the tumor sites. It has been reported extensively that exogenously infused IL2 can enhance destructive immune responses against malignant tumors and visceral metastasis. This finding has been demonstrated in a xenograft metastatic sarcoma mouse model and in patients with metastatic melanoma who were systemically administered recombinant IL2 or received adoptively transferred tumor-reactive T cells (Kochenderfer et al., 2012; Lo et al. 2010 Clin Cancer Res 16, 2769-2780; Porter et al., 2011 N Engl J Med 365, 725-733; Rosenberg et al., 1985a N Engl J Med 313, 1485-1492; Rosenberg et al., 1985b J Exp Med 161, 1169-1188; Rosenberg et al., 2011 Cancer Res 17, 4550-4557).

As a type I cytokine, IL2 may be one of the most important cytokine lost during exhaustion. IL2 plays a pivotal role in clonal expansion and persistence of virus- and tumor-reactive T cells and in their effector activity (Liao et al., 2013 Immunity 38, 13-25; Rosenberg et al., 1985b, supra). The demonstrated therapeutic benefit of exogenously supplemented IL2 in humans and in model systems of cancer and infections is one indicator of this impact of exhaustion that hampers T cells' ability to generate this same effector molecule (Blattman et al., 2003 Nat Med 9, 540-547; Emtage et al., 2008 Clin Cancer Res 14, 8112-8122; Liao et al., 2013, supra; Lo et al., 2010, supra; Rosenberg et al., 1985b, supra). Similarly, the effectiveness of antibodies against the checkpoint receptors to restore T cell function and generate clinical responses is additional testimony to the relevance of exhaustion to clinical disease (Barber et al., 2006 Nature 439, 682-687; Nguyen and Ohashi, 2015 Nat Rev Immunol 15, 45-56). Lastly, there has been an appreciation that a therapeutic synergy may be derived by concurrently addressing the two axes of cytokines and checkpoint receptors (West et al., 2013 J Clin Invest 123, 2604-2615).

Despite advances in the molecular and phenotypic characterization of exhausted T cells, the molecular mechanism (initiation and progression) of exhaustion and associated loss of IL2 in vivo remains poorly understood.

T cell adoptive immunotherapy is a promising tool to cure metastatic malignant cancers and chronic infections. An early innovation was the use of tumor infiltrating lymphocytes (TILs) as a cancer immunotherapy (Hinrichs and Rosenberg, 2014 Immunol Rev 257, 56-71). TILs are isolated from tumors, extensively expanded ex vivo and infused back into cancer patients to generate antitumor reactivity. Despite an initial robust antitumor reactivity observed in patients, infused TILs succumb to exhaustion, as marked by limited persistence in vivo, reducing their overall potential to suppress tumors. Exhaustion in TILs has been demonstrated in human melanoma and in mice bearing solid tumors (Baitsch et al., 2011 J Clin Invest 121, 2350-2360; Olurinde et al., 2011 Cell Mol Immunol 8, 415-423).

Likewise, genetically modified chimeric antigen receptor T cells (CAR-T) have been applied. CAR-T cells are generated by genetically modifying T cell receptors with an antigen binding domain of an immunoglobulin (Ig) recognizing tumor associated antigen. CAR-T cells exhibit antibody-redirected and MHC-independent cancer cell killing (Curran et al., 2012 J Gene Med 14, 405-415; Ma et al., 2002 Cancer Chemother Biol Response Modif 20, 315-341). In particular, CD19 CAR-T cells have shown remarkable success in eradicating chronic lymphocytic leukemia in clinical trials (Porter et al., N Engl J Med 365, 725-733 2011). However, success of the CD19-CAR has rarely been replicated in CAR-Ts developed to treat solid tumors (Junghans, 2017 Cancer Gene Ther 24, 89-99; Kershaw et al., 2006 Clin Cancer Res 12, 6106-6115; Lamers et al., 2013 Mol Ther 21, 904-912; Park et al., 2007 Mol Ther 15, 825-833; Till et al., 2012 Blood 119, 3940-3950). Data obtained from anti-CEA CAR T cells showed loss of IL2 secretion upon repeated stimulation with CEA+ tumors (Emtage et al., 2008, supra). Similarly, TCR transfer T cells have been applied with clinical responses in cancer but which were not sustained (Parkhurst et al., 2011 Mol Ther 19, 620-626). These solid tumor treatments with engineered T cells have likewise been hampered by exhaustion (Long et al., 2015 Nat Med).

In response to these problems, clinical blockade of checkpoint receptors PD1 and LAG3 and their ligands have shown clinically promising results across a range of solid tumors (Nguyen and Ohashi, 2015 Nat Rev Immunol 15, 45-56; Rajan et al, 2016 Hum Vaccin Immunother 12, 2219-2231; Menon et al, 2016). However, only a fraction of patients respond to checkpoint inhibitor treatment. Therefore, there is an unmet need for a breakthrough in the understanding of the mechanism of anti-tumor and anti-chronic infection T cell dysfunction and also an alternative approach to targeting of check point receptors for human immunotherapies.

Chronic infections subject to T-cell exhaustion include viral infections and microorganisms that grow inside human cells. T cells cannot directly attack viruses or microorganisms; they kill by only by recognizing MHC-presented foreign peptide on host cells and only nucleated host cells (not red cells) express MHC. Whereas many infections may invade cells, those that can live without cell invasion are called facultative, and these infections cannot be cured by T cells killing only the infected cells. On the other hand, those infectious agents that are obligate parasites, e.g., *M. leprae, leishmania*, can potentially be cured by a potent T cell response that kills the host cells.

Compositions and methods for reducing or preventing T-cell exhaustion are needed.

SUMMARY

Provided herein are compositions and methods for improving immune system function. In particular, provided herein are compositions, methods, and uses of YY1 and EZH2 inhibitors for preventing and reversing T-cell exhaustion (e.g., for use in immunotherapy).

For example, provided herein is a method of preventing or reversing T-cell exhaustion in a subject, comprising: a) downregulating or knocking out the gene expression of YY1 or EZH2; or b) inhibiting the protein product of the expression of YY1or EzH2, in said T-cells. Also provided herein are methods and uses for preventing or reversing T-cell exhaustion in a subject, comprising: a) contacting T cells with a YY1 and/or EZH2 inhibitor to generate therapeutic T cells; and b) administering the therapeutic T cells to the subject. In some embodiments, the administering further comprises administering a YY1 and/or EZH2 inhibitor to the subject. In some embodiments, the EZH2 and/or YY1 inhibitor is selected from, for example, a nucleic acid (e.g., siRNA, shRNA, miRNA or an antisense nucleic acid)), a vector (e.g., for generating a gene knock-out), a small molecule, a peptide, or an antibody. In some embodiments, the small molecule EZH2 inhibitor is, in non-limiting examples, 3-Deazaneplanocin A (DZNep), EPZ005687, GSK503, GSK343, GSK126, EI1, or CPI-169 (available from ApexBio, Houston, Tex.) or other inhibitors). In some embodiments, the YY1 inhibitor is a nucleic acid (e.g., an siRNA, shRNA, miRNA and an antisense nucleic acid). In some embodiments, the YY1 inhibitor is on a vector that expresses a siRNA, shRNA or a microRNA to YY1. In some embodiments, the EZH2 and/or YY1 gene is knocked out. In some embodiments, the YY1 inhibition is done by inhibiting the activity of one or more upstream modulators of YY1 (e.g., AKT, MEKK1, MKK3/6, MKK4/7, p38, JNK, ATF2, or cJUN (e.g., using one or more of MAPKp38-SB202190, JNK-SP600125, MEK1-PD98059, or MEK1/2-inhibitor III)). In some embodiments, the T cells are autologous or heterologous to the subject. In some embodiments, the contacting is performed ex vivo or in vitro. In some embodiments, T-cells are expanded ex vivo prior to the contacting. In some embodiments, the T cell exhibits exhaustion. In some embodiments, YY1 and/or EZH2 is overexpressed in the T cells (e.g., relative to T-cells from non-diseased patients or T-cells from the patient that are not reactive with the disease antigens or not chronically stimulated by other self or foreign antigens). In some embodiments, the T cell comprises a chimeric antigen receptor (CAR). In some embodiments, the method treats cancer or chronic infectious disease. In some embodiments, the chronic infectious disease is a chronic viral disease (e.g., HIV or HBV) or chronic diseases caused by intracellular organisms (e.g., bacteria such as *M. leprae*, parasites such as *Leishmania* or other intracellular parasitic organism). In some embodiments, the T-cell is a tumor antigen reactive T-cell or a tumor infiltrating lymphocyte. In some embodiments, the T-cell is a viral or intracellular microorganism antigen reactive T-cell.

Certain embodiments provide a method or use of preventing or reversing T-cell exhaustion in a subject, comprising: a) isolating T-cells from a subject; (b) expanding the T-cells ex vivo; c) contacting the T cells with a YY1 and/or EZH2 inhibitor to generate therapeutic T cells; and d) administering the therapeutic T cells to the subject. In some embodiments, the contacting is after or during the expansion step. In some embodiments, the method further comprises the step of administering a YY1 and/or EZH2 inhibitor to the subject prior to, during, or after administration of the therapeutic T-cells.

In some embodiments, the present disclosure provides a method or use of treating cancer or chronic infectious disease in a subject, comprising: a) assaying T-cells reactive with relevant antigens from the subject for the presence or level of EZH2 and/or YY1 expression; and b) administering an EZH2 and/or YY1 inhibitor when high expression of EZH2 and/or YY1 relative to the level in a sample from a subject that does not have cancer or a chronic infectious disease. In some embodiments, the T cell exhaustion marker is PD1. In some embodiments, the antigens are from cancer cells or chronically infected cells that the T-cell sample are reactive with.

The present disclosure is not limited to treatment of particular cancers. In some embodiments, the cancers are cancers where T-cell exhaustion prevents the immune system from eradicating the cancer. Examples of such cancers include, but are not limited to, melanoma, non-small cell lung cancer, transitional cell carcinoma and Hodgkin's lymphoma.

The present disclosure is not limited to treatment of particular chronic infectious diseases. In some embodiments, the chronic infectious diseases are diseases where T-cell exhaustion prevents the immune system from eradicating the infection. In some embodiments, the chronic infectious diseases are diseases caused by microorganisms that reside inside human cells (e.g., diseases caused by chronic intracellular microorganisms). Examples include, but are not limited to, intracellular dwelling bacteria and parasites (e.g., HIV, HBV, CMV, EBV, HCV, *M. leprae*, or *Leishmania*).

Further embodiments provide a method of treating a chronic infectious disease in a subject, comprising: administering a EZH2 and/or YY1 inhibitor to the subject.

Additional embodiments provide a composition, comprising: T-cells comprising a YY1 and/or EZH2 inhibitor (e.g., synthetic or exogenous inhibitor). In some embodiment, the YY1 and/or EZH2 inhibitor is an siRNA, shRNA, miRNA or antisense nucleic acid (e.g., provided on an autonomously replicating nucleic acid such as a vector or retroviral vector). In some embodiments, the T cell comprises a chimeric antigen receptor (CAR).

Certain embodiments provide a composition, comprising: T cells lacking a functional YY1 and/or EZH2 gene. In some embodiments, the YY1 and/or EZH2 gene is knocked out. In some embodiments, the YY1 gene is knocked out.

In some embodiments, the present disclosure provides a method of treating cancer or chronic infectious disease in a subject, comprising: a) identifying said subject as having a cancer-type or infection-type as being associated with T cell exhaustion when i) the type of cancer is melanoma, transitional cell carcinoma, non-small cell lung cancer, renal cell carcinoma or other cancer associated with T cell exhaustion; ii) the type of infection is HIV or HBV or other infection associated with T cell exhaustion; iii) the type of cancer is non-small cell lung cancer, transitional cell carcinoma, or other cancer that is responsive or improves or is cured by addressing the checkpoint receptor axis of exhaustion with anti-checkpoint receptor therapy; iv) the type of cancer is melanoma or renal cell carcinoma or other cancer that is responsive or improves or is cured by addressing the cytokine axis of exhaustion with interleukin 2 or other cytokine supplementation therapy; v) the type of infection is HIV or HBV or other infection that is responsive or improves or is cured by addressing the checkpoint receptor axis of exhaustion with anti-checkpoint receptor therapy; or vi) the type of infection HIV or HBV or other infection that is responsive or improves or is cured by addressing the cytokine axis of exhaustion with interleukin 2 or other cytokine supplementation therapy; and b)administering an agent that inhibits YY1 expression or activity and/or an agent that inhibits EZH2 expression or activity to the subject.

Additional embodiments are described herein.

DESCRIPTION OF THE FIGURES

FIG. 13 shows that IL2 promoter contains YY1 binding site.

FIG. 17 shows transcription factor consensus sites in exhaustion related promoters. (A-D) Promoter sequences match in Transfac database (Biobase) for TF binding sites using cutoffs to minimize false positive matches. Consensus sites are shown in PD1, Lag3, Tim3 and YY1 promoters along with scores. (E) Table shows distance of key TF binding sites from respective transcription start sites (TSS).

DEFINITIONS

Figure 1:
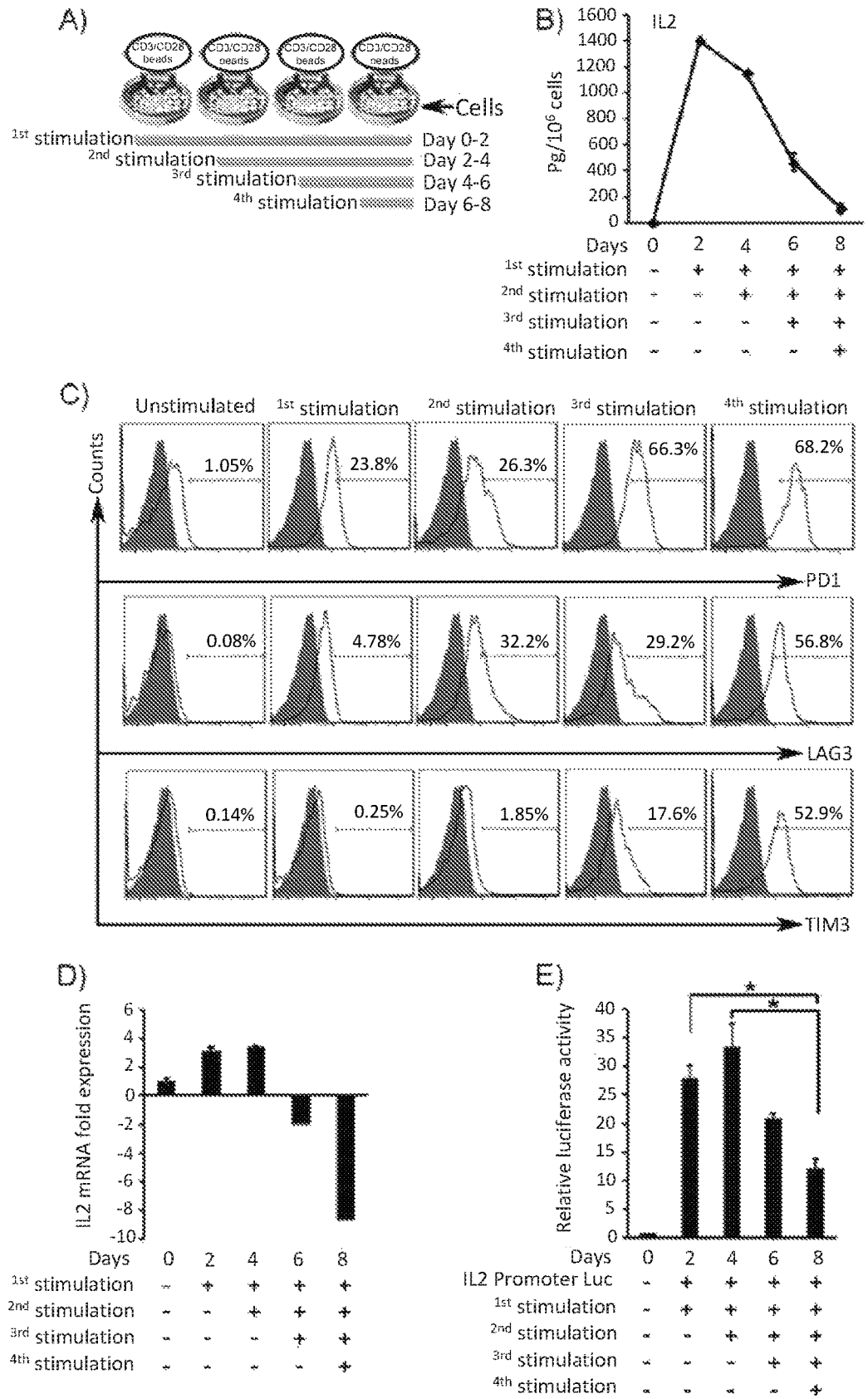
FIG. 1 shows that persistent T cell activation in vitro induces IL2 shutdown and checkpoint receptor elevation. (A) Schematic depicting repeat stimulation model. (B) ELISA shows high secretion then decline of IL2 production after repeated stimulations. (C) Flow cytometry of re-stimulated CD4 T cells shows increasing expression of exhaustion markers, PD1, Lag3 and Tim3. (D) qRT-PCR and (E) IL2 promoter luciferase assay in CD4 T cells shows fold-change of IL2 mRNA and promoter activity after re-stimulations. Four replicates performed per assay; data from one of three representative experiments. *$p<0.05$.

To facilitate an understanding of the present disclosure, a number of terms and phrases are defined below:

As used herein, the term "T cell exhaustion" refers to a state of T cells (e.g., in vivo, ex vivo, or in vitro) wherein T cells exhibit a stepwise and progressive loss of T-cell functions and can, in some embodiments, culminate in the physical deletion of the responding cells (e.g., "T-cell depletion"). Exhaustion occurs, for example, during chronic infection, in malignant tumors and during T cell based cancer immunotherapy (Balkhi et al., 2015, supra; Virgin et al., 2009 138, 30-50; Wherry, 2011 Nat Immunol 12, 492-499).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of cancer. A subject suspected of having cancer may also have one or more risk factors. A subject suspected of having cancer has generally not been tested for cancer. However, a "subject suspected of having cancer" encompasses an individual who has received a preliminary diagnosis but for whom a confirmatory test has not been done or for whom the level or severity of cancer is not known.

As used herein, the term "subject diagnosed with cancer" refers to a subject who has been tested and found to have cancer. As used herein, the term "initial diagnosis" refers to a test result of initial disease that reveals the presence or absence of disease.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of a compound (e.g., a compound described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., EZH2 or YY1 inhibitor compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, or ex vivo.

As used herein, the term "toxic" refers to any detrimental or harmful effects on a cell or tissue as compared to the same cell or tissue prior to the administration of the toxicant.

DETAILED DESCRIPTION OF THE DISCLOSURE

Provided herein are compositions and methods for improving immune system function. In particular, provided herein are compositions, methods, and uses of YY1 and EZH2 inhibitors for preventing and reversing T-cell exhaustion (e.g., for use in immunotherapy).

YY1 is a ubiquitous and multi-functional zinc-finger transcription factor that regulates diverse cellular functions, including B cell development, proliferation, differentiation and tumorigenesis (Gordon et al., 2006 Oncogene 25, 1125-1142; Liu et al., 2007 Genes Dev 21, 1179-1189). YY1 regulates both positively and negatively after binding to the consensus sequence 5'-CCGCCATNTT-3'(SEQ ID NO: 37) in the promoters of these genes (Thomas and Seto, 1999 Gene 236, 197-208).

Ezh2 is a component of the PRC2 protein complex that possess histone lysine methyltransferase activity (HKMT). This activity is associated with trimethylation of H3 lysine 27 (H3K27me3), which leads to the transcriptional repression of genes (Caretti et al., 2004 Genes Dev 18, 2627-2638). T cell immunotherapy remains the most attractive treatment option to cure malignancy, as confirmed by the dramatic success of CD19 CAR-T cells in hematological malignancies (Lee et al., 2015 Lancet 385, 517-528; Maude et al., 2015 Blood 125, 4017-4023). Exhaustion, however, remains a limiting factor in attaining the full potential of T cell immunotherapy (Long et al., 2015, supra) in part due to a lack of knowledge about signaling pathways regulating exhaustion. The results described herein provide new insights into the process of T cell exhaustion in vivo and in CAR-T cells, and the compelling evidence of a central role of YY1/Ezh2 in mediating this process through IL2 shutdown.

Figure 19:
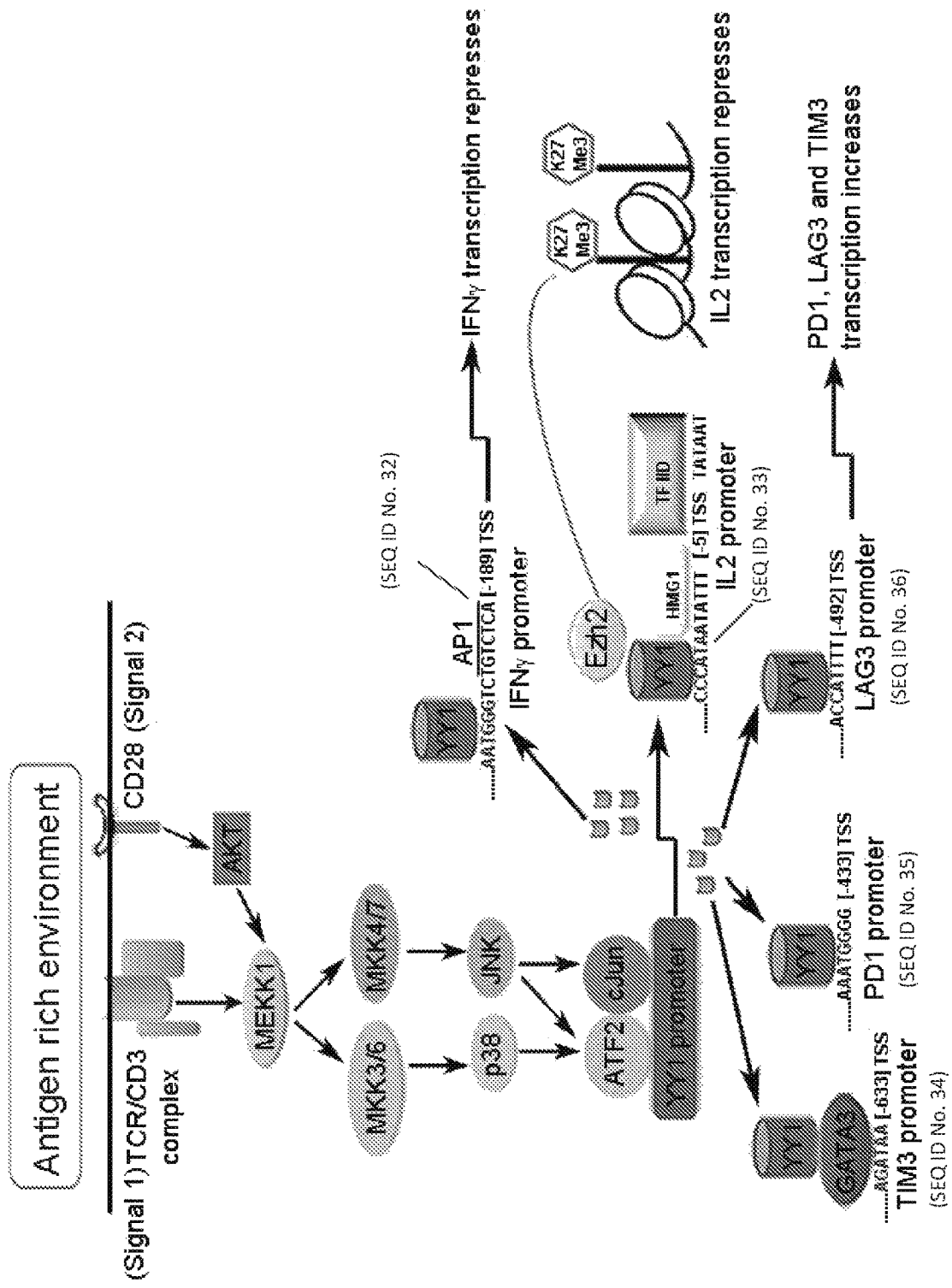
FIG. 19 shows a summary diagram of exhaustion regulation.
Figure 21:
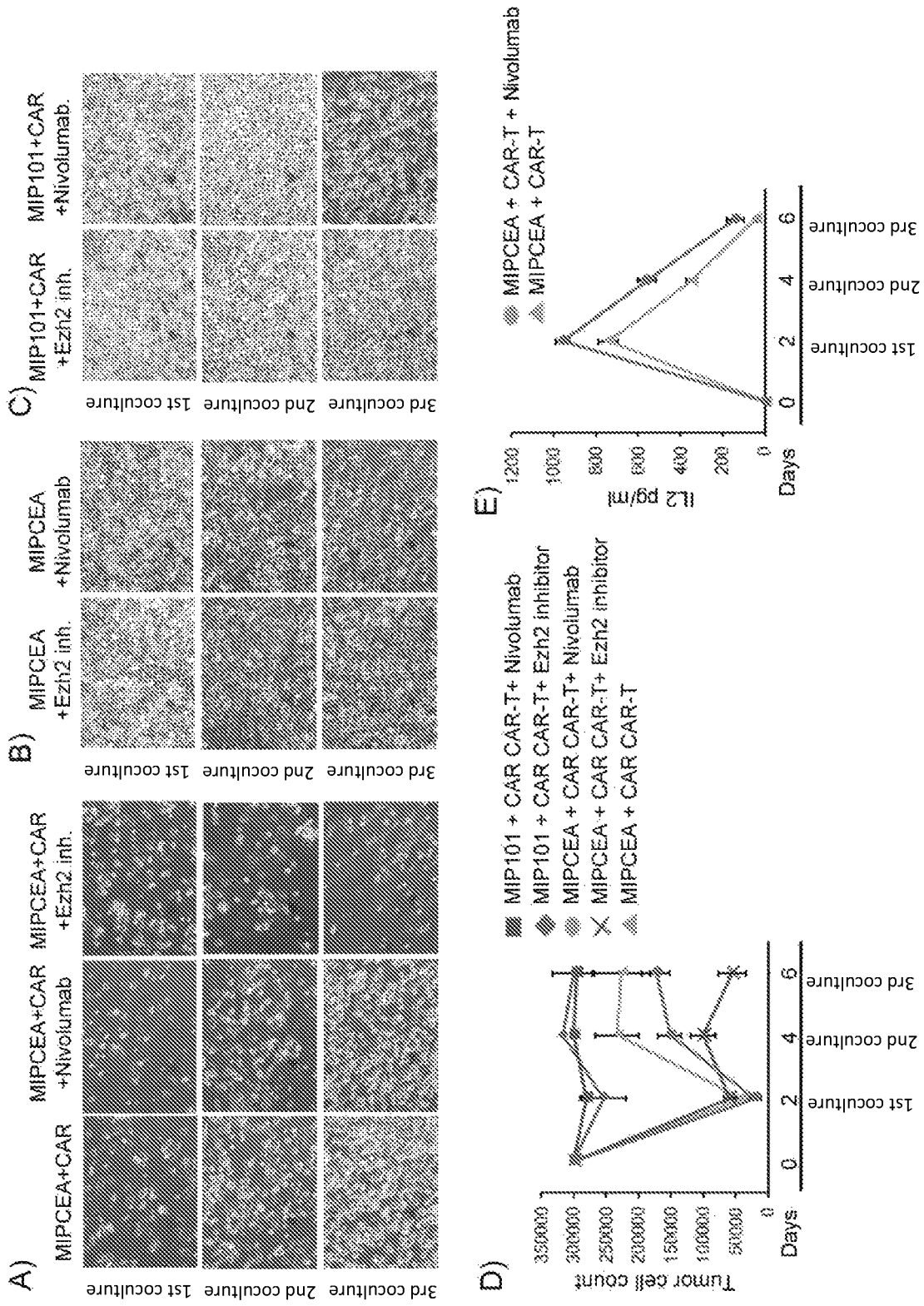
FIG. 21 shows rescue from cytotoxic exhaustion with nivolumab compared to Ezh2. (A) $2^{nd}$ generation CAR-T cells with ~50% modification were cocultured 3 times for two days with MIPCEA cell line either in continued presence of nivolumab (20 µg/ml) or Ezh2 inhibitor (10 nm) or no additive and imaged. (B) MPI-CEA cell line incubated with inhibitors alone showed no toxicity. (C) Antigen-negative MIP101 cells were not killed by CAR-T cells in presence of exhaustion inhibitors. (D) Cell counts obtained from experiment in (A-C), showing partial rescue of killing effect with nivolumab and more complete rescue with Ezh2 inhibitor. Three replicates per assay; representative of three experiments. (E) IL2 ELISA shows high initial IL2 production in MIPCEA/CAR-T cell cocultures in presence and absence of nivolumab that declined in parallel when CAR T cells were re-exposed to second and third batches of target tumor cells.

Results described herein show that persistent activation of signal 1+2 in T cells is required both for the upregulated expression of YY1 and Ezh2 and the progression to exhaustion. Signal 1 or signal 2 alone is insufficient to give rise to either an increased expression of YY1 and Ezh2 or chronic exhaustion. In the exhaustion settings, signal 2, in addition to TCR signaling, may be acting through AKT as well (FIG. 5B). It is further contemplated that YY1 recruits Ezh2 to the IL2 promoter to epigenetically silence IL2 transcription in vivo to induce exhaustion against reactive-tumors (FIGS. 21 & 19). Melanoma is classically associated with exhausted T cells (TILs, tumor infiltrating lymphocytes (Baitsch et al, 2011, supra)). The majority of human malignant melanoma tumors express B7.2 that can interact with T cell CD28 to provide signal 2. The presence of highly elevated levels of YY1 in T cells infiltrating metastatic melanoma may be driven by signal 1+2 and may represent a central feature associated with IL2 shutdown and exhaustion.

Figure 6:
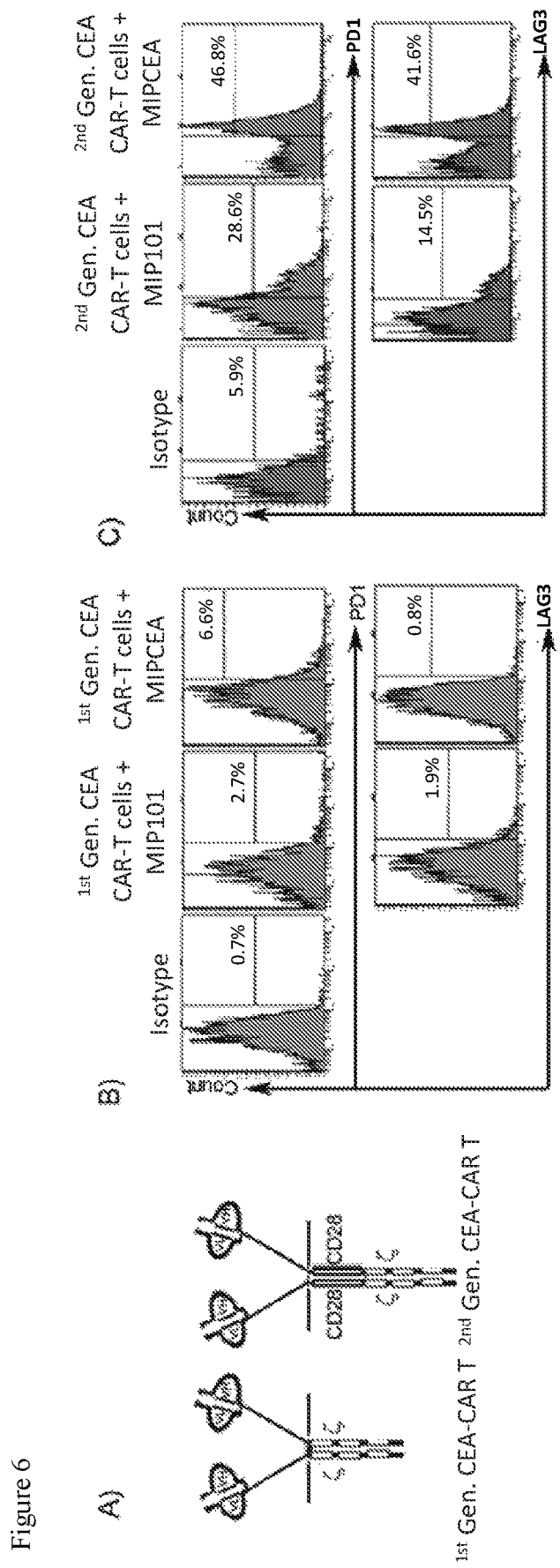
FIG. 6 shows Functional assessment of T cell exhaustion. (A) Design of CAR-T cells. (B, C) Increased expression of checkpoint markers with restimulation only on $2^{nd}$ generation CAR-T cells. (D) IL2 ELISA shows high initial IL2 and then decline in MIPCEA/CAR-T cell cocultures. (E) Functional exhaustion shown by live images of MIPCEA target cells before and after coculture with CAR-T cells. (F) IL2 ELISA as in (D) except coculture performed in presence of Ezh2 inhibitor, showing sustained IL2. (G) Reversal of functional exhaustion shown by live images of MIPCEA and control MIP101 target cells after coculture with CAR-T cells in presence of Ezh2 inhibitor with or without anti-IL2 antibody that blocks exhaustion reversal. (H) Cell counts obtained from experiment in (E) and (G). Three replicates per assay; representative of three experiments.
Figure 6:
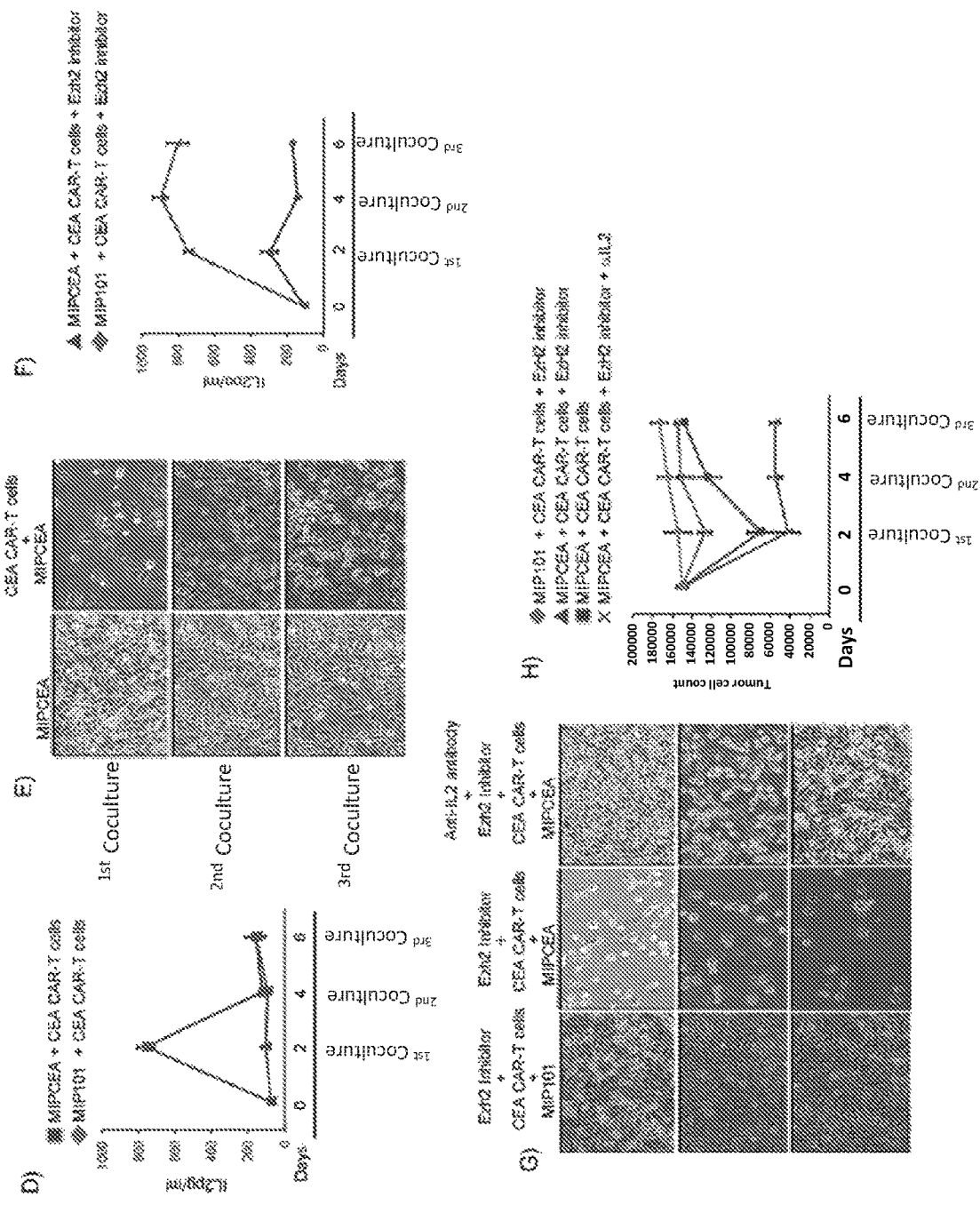

Accordingly, clinical application of these results improves adoptive immunotherapy through the development of interventions that resist IL2 shutdown. IL2 shutdown is consistently observed in antigen-specific T cells and gene modified T cells used in adoptive immunotherapy clinical trials (Atkins, 2000 Sci Am 6 Suppl 1, S8-10; Klapper et al., 2008 Cancer 113, 293-301; Smith et al., 2008 Clin Cancer Res 14, 5610-5618). Patients may benefit from exogenously supplemented systemic IL2 therapies, as it has proven to be advantageous to the treatment of solid tumors such as melanoma and renal cell cancers (Atkins, 2000, supra; Klapper et al., 2008, supra; Smith et al., 2008, supra). Similar conclusions have been derived in CAR-T models (Emtage et al, 2008 Clin Cancer Res 14, 8112-8122; Katz et al., 2015 Clin Cancer Res 21, 3149-3159; Lo et al., 2010, supra). Thus, if IL2 decline is resisted in T cells infiltrating metastatic malignant tumors, antigen-specific T cells may continue to kill tumor cells and generate memory response, obviating the need for systemic IL2 therapies that although advantageous are associated with significant toxicity and cost. Therefore, the depletion of YY1 or blocking Ezh2 activity is provided to prevent IL2 shutdown in tumor infiltrating lymphocytes (TILs) or in CAR T cells used in cancer immunotherapy (Hinrichs and Rosenberg, 2014, supra). An Ezh2 inhibitor in combination with CEA-CAR T cells was tested in experiments described herein. This cell-permeable GSK126 analogue acts as a selective potent inhibitor of both Ezh1 and Ezh2, is competitive with cofactor SAM, and competitively blocks Histone H3-K27 trimethylation (Konze et al., 2013). The results show that Ezh2 inhibitor helped CEA-CAR T cells to resist exhaustion against reactive-tumors by sustaining autogenous IL2 production that overrides the inhibitory signals emanating from inhibitory receptor molecules (FIG. 6).

The results also revealed the previously unknown role of YY1 and Ezh2 in IL2 shutdown in activated T cells in vitro. The repeated-stimulation model described herein helped to reveal association between YY1 and Ezh2 in relation with exhaustion and IL2 repression.

Figure 2:
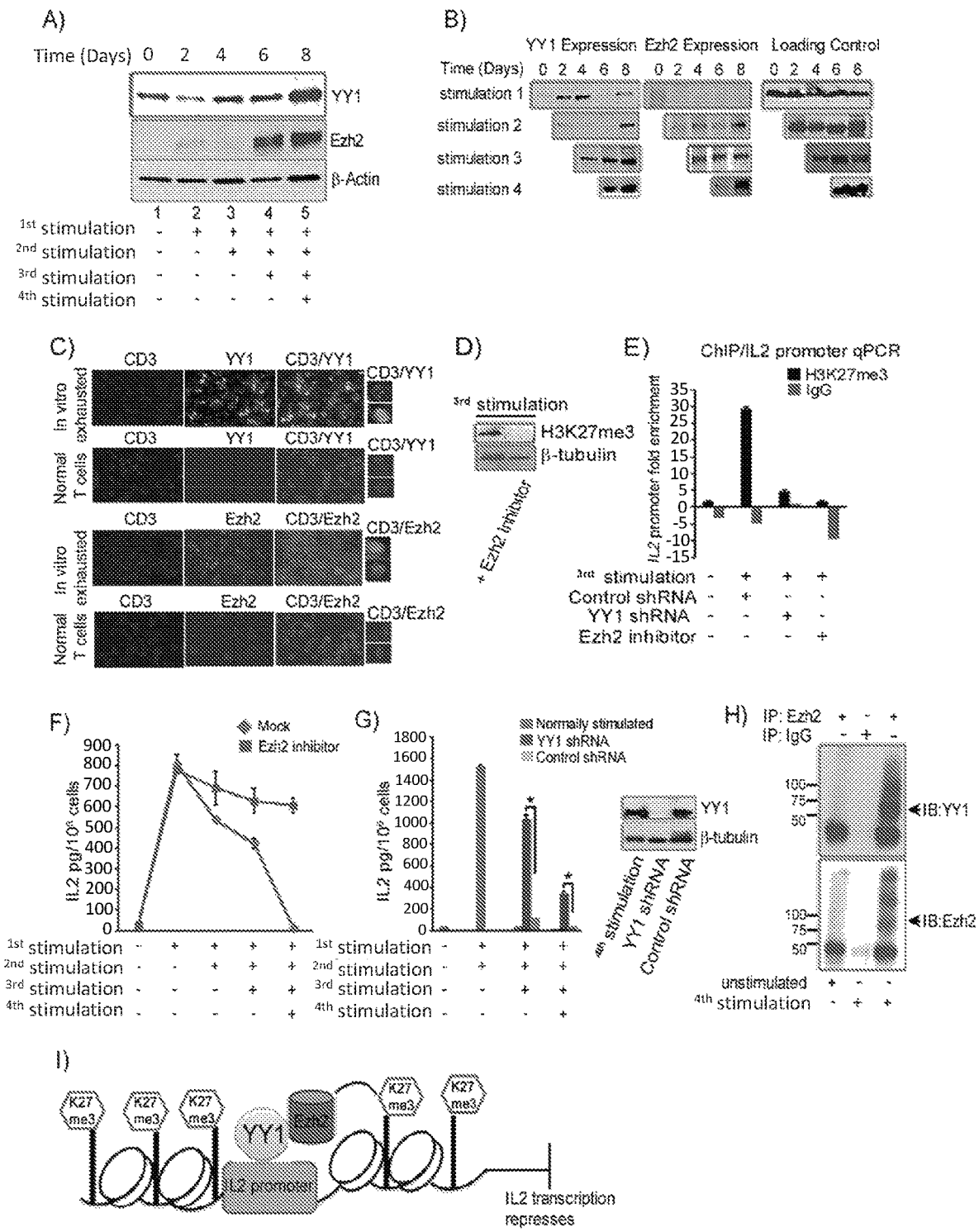
FIG. 2 shows that persistent T cell activation upregulates YY1 and Ezh2 to epigenetically silence IL2. (A) Western blots show increasing expression of YY1 and Ezh2 after re-stimulation of CD4 T cells. β-actin is loading control. (B) More YY1 and Ezh2 from persistent activation by comparing 1-4 stimulations with results assessed until 8 days as in (A). (C) Immunofluorescence (IF) performed on 4-times stimulated exhausted T cells and unstimulated PBMCs showing YY1 and Ezh2 expression. Right panels show magnified single cell single positive for CD3 or double positive for CD3/YY1 and CD3/Ezh2. (D) Western blot shows decreased levels of H3K27me3 with Ezh2 inhibitor. (E) qPCR for IL2 promoter shows high H3K27me3 methylation with recurrent stimulation that is decreased with Ezh2 inhibitor or YY1 shRNA. Chromatin immunoprecipitation (ChIP) with anti-H3K27me3 antibody or IgG in twice-stimulated CD4 T cells, transduced before 3rd stimulation with plasmid for control-shRNA (lane 2) or YY1 shRNA (lane 3), or maintained from day 0 in presence of Ezh2 inhibitor (lane 4). (F) ELISA shows sustained IL2 production from CD4 T cells stimulated repeatedly in vitro without or with Ezh2 inhibitor. (G) ELISA assay shows recovered IL2 production from exhausted T cells with YY1 shRNA. (H) Co-IP confirms YY1 interaction with Ezh2 in repeatedly stimulated T cells. IP was with Ezh2 antibody and the blot was probed with YY1 (upper panel) or Ezh2 antibody (bottom panel). (I) Model showing YY1 acting in association with Ezh2 to repress IL2 transcription. Graphs in (E)-(G) are from a minimum of three replicates; assays representative of at least three experiments. *$p<0.05$.

YY1 is readily inactivated in therapeutic T cells (TIL and CAR-T) with RNAi, as shown in FIG. 2G. In some embodiments, small molecule direct inhibitors to YY1 are provided. In some embodiments, small molecule inhibitors can act at points along the p38MAPK/JNK2 pathway to block YY1 transcription (FIG. 5C).

Ezh2 can be directly inhibited with small molecules systemically (e.g., those that have shown favorable safety profiles in early stage clinical trials primarily in Ezh2-expressing lymphomas (Ribrag, et al., *Eur J Cancer* 50, 197 (2014)). In some embodiments, Ezh2 activity is interrupted in therapeutic T cells with RNAi. Ezh2 has attracted interest as a cancer target due to its overexpression and mutational hyperactivity in some tumors (Kim and Roberts, *Nat Med* 22, 128-134, (2016). In some embodiments, targeting of Ezh2 or YY1 in the current context is solely for the directed treatment of exhausted T cells, irrespective of tumor Ezh2 gene expression, with broad implications for infections as well as cancer.

The experiments described herein also determined the effect of selectively blocking the p38MAPK/JNK signaling pathway on antitumor responses of T cells in vivo. The presence of activated phospho-cJun (Ser63/73) in exhausted T cells (FIG. 7B) supports the hypothesis that constitutive p38MAPK/JNK signaling represses IL2 production indirectly by activating YY1 through cJun/ATF2 dimer. The simultaneous rise of Ezh2 along with PD1, LAG3 and TIM3 may also support regulation of these genes by YY1 transcription factor. Therefore, their promoter sequences were searched for the possible transcription factor matches using Transfac database (Biobase) including in the search cutoffs to minimize false positive matches and allowed only high quality matrices. Data analysis revealed PD1 and LAG3 possess consensus binding sites for YY1 (FIG. 17A-B), showing regulation of PD1 and LAG3 gene directly by YY1, whereas Ezh2 and TIM3 do not possess YY1 binding sites. These data show that YY1 may intrinsically act as activator of PD1 and LAG3 in T cells undergoing exhaustion, while its IL2 repressor functions may require association with Ezh2. Interferon-gamma repression by YY1 is direct and does not require Ezh2. GATA3 association with TIM3 was postulated to allow activation of the TIM3 by YY1.

Accordingly, provided herein are compositions and methods for preventing T cell exhaustion. In some embodiments, provided herein are compositions and methods for enhancing immunotherapies (e.g., in cancer and infectious disease) by preventing T cell exhaustion. In some embodiments, EZH2 and/or YY1 expression and/or activity are prevented in order to prevent or reduce T cell exhaustion. In some embodiments, EZH2 and/or YY1 activity is inhibited directly. In other embodiments, upstream regulators of YY1 and/or EZH2 activity are inhibited (See e.g., FIG. 19 for a diagram of the exhaustion-related YY1/EZH2 pathways). Exemplary EZH2 and YY1 inhibitors are described below.

I. Inhibitors

In some embodiments, the EZH2 and/or YY1 inhibitor is selected from, for example, a nucleic acid (e.g., siRNA, shRNA, miRNA or an antisense nucleic acid), a small molecule, a peptide, or an antibody.

Figure 5:
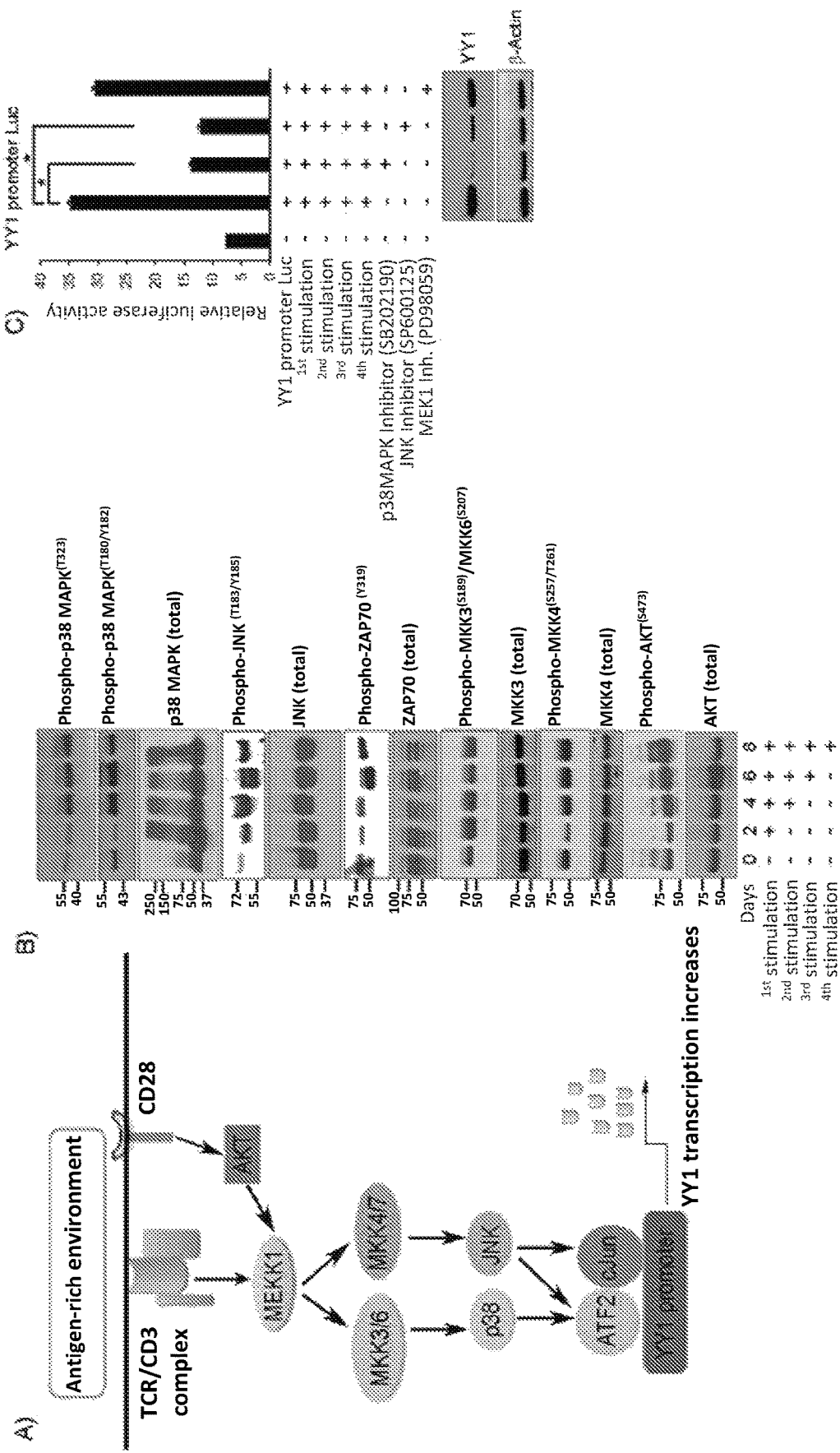
FIG. 5 shows p38MAPK/JNK signaling pathway regulates YY1 expression. (A) Model depicting p38MAPK/JNK signaling to cJun/ATF2 to regulate YY1 in T cells exposed to antigen-rich environment. (B) Western blots show increased phosphorylation of kinases in p38MAPK/JNK pathway with T cell restimulation. (C) YY1 is suppressed by inhibitors to p38 and JNK by reporter assay (upper) and by Western blot (lower). Three replicates per assay; representative of three experiments. *$p<0.05$.

In some embodiments, inhibitors are selected to block upstream signaling molecules of YY1 such as, for example, MAPKp38 inhibitor (SB202190), JNK inhibitor (SP600125), AKT inhibitor (wortmannin), MKK3/6 and MKK4/7 inhibitors (See e.g., FIG. 5).

In some embodiments, the EZH2 small molecule inhibitor is, for example,

3-Deazaneplanocin,

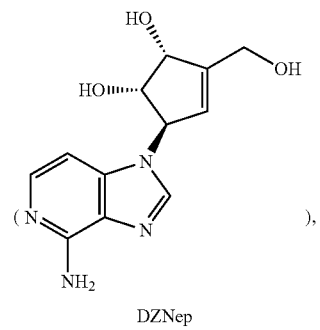

DZNep

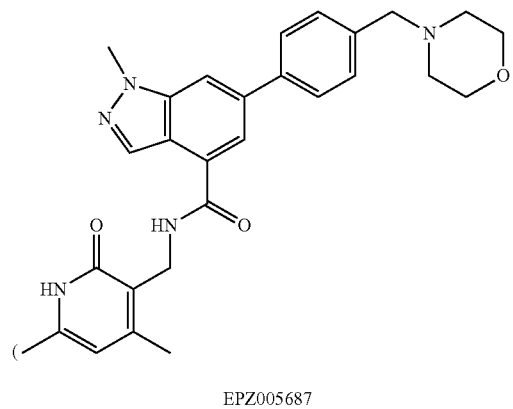

EPZ005687

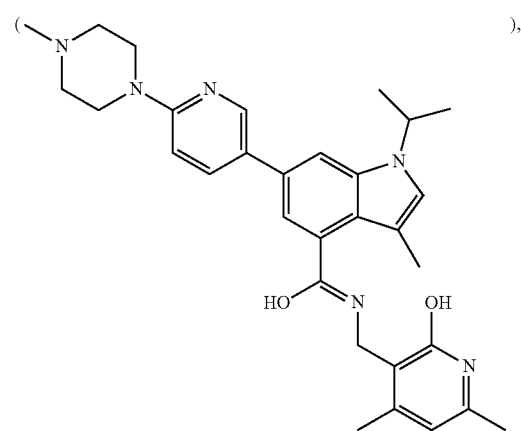

GSK503

-continued

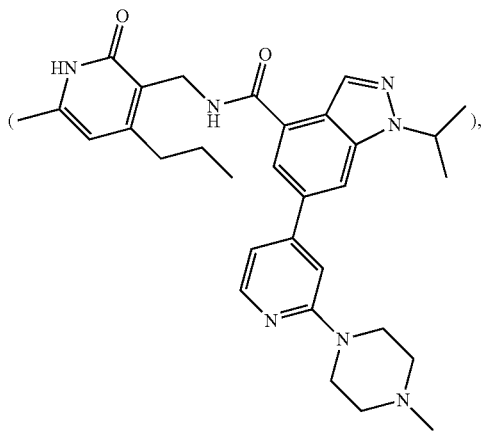

GSK343

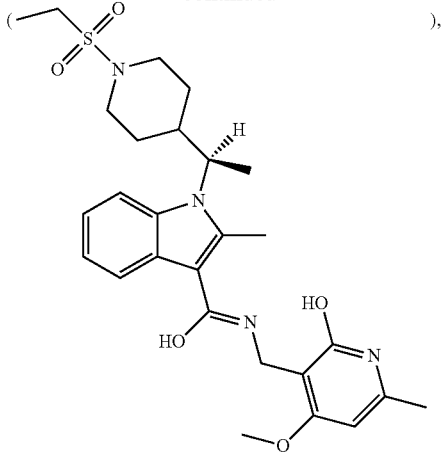

CPI-169

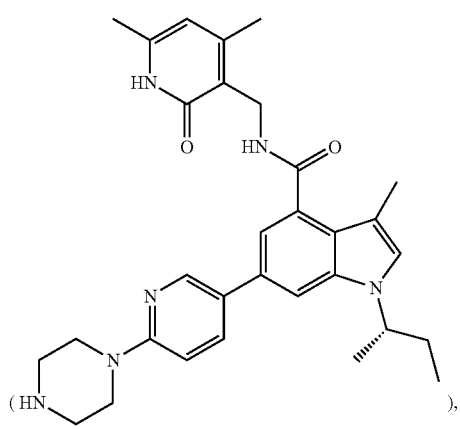

GSK126

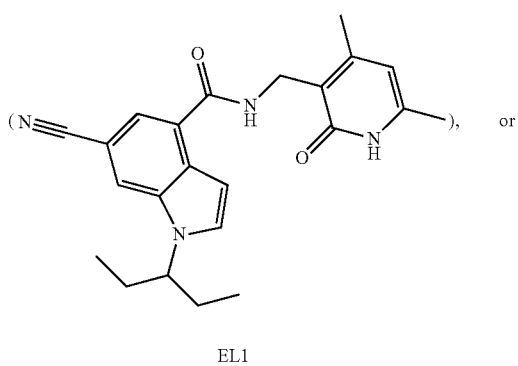

EL1 all of which are commercially available (e.g., from ApexBio, Houston, Tex.).

In some embodiments, the EZH2 and/or YY1 inhibitor is a nucleic acid. Exemplary nucleic acids suitable for inhibiting EZH2 and/or YY1 (e.g., by preventing expression of EZH2 and/or YY1) include, but are not limited to, antisense nucleic acids and RNAi. In some embodiments, nucleic acid therapies are complementary to and hybridize to at least a portion (e.g., at least 5, 8, 10, 11, 12, 13, 14, 15, 16, 17, 18, 19, or 20 nucleotides) of EZH2 (GenBank Accession number U61145.1) and/or YY1 (GenBank Accession number NM_003403).

In some embodiments, compositions comprising oligomeric antisense compounds, particularly oligonucleotides are used to modulate the function of nucleic acid molecules encoding EZH2 and/or YY1, ultimately modulating the amount of EZH2 and/or YY1 expressed. This is accomplished by providing antisense compounds that specifically hybridize with one or more nucleic acids encoding EZH2 and/or YY1. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is decreasing the amount of EZH2 and/or YY1 proteins in the T-cell.

In some embodiments, nucleic acids are RNAi nucleic acids. "RNA interference (RNAi)" is the process of sequence-specific, post-transcriptional gene silencing initiated by a small interfering RNA (siRNA), shRNA, or microRNA (miRNA). During RNAi, the RNA induces degradation of target mRNA with consequent sequence-specific inhibition of gene expression.

In "RNA interference," or "RNAi," a "small interfering RNA" or "short interfering RNA" or "siRNA" or "short hairpin RNA" or "shRNA" molecule, or "miRNA" an RNAi (e.g., single strand, duplex, or hairpin) of nucleotides is targeted to a nucleic acid sequence of interest, for example, YY1 or EZH2.

An "RNA duplex" refers to the structure formed by the complementary pairing between two regions of a RNA molecule. The RNA using in RNAi is "targeted" to a gene in that the nucleotide sequence of the duplex portion of the RNAi is complementary to a nucleotide sequence of the targeted gene. In certain embodiments, the RNAi is are targeted to the sequence encoding EZH2 and/or YY1. In some embodiments, the length of the RNAi is less than 30 base pairs. In some embodiments, the RNA can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the RNAi is 19 to 32 base pairs in length. In certain embodiment, the length of the RNAi is 19 or 21 base pairs in length.

In some embodiments, RNAi comprises a hairpin structure (e.g., shRNA). In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase.

As used herein, Dicer-substrate RNAs (DsiRNAs) are chemically synthesized asymmetric 25-mer/27-mer duplex RNAs that have increased potency in RNA interference compared to traditional RNAi. Traditional 21-mer RNAi molecules are designed to mimic Dicer products and therefore bypass interaction with the enzyme Dicer. Dicer has been recently shown to be a component of RISC and involved with entry of the RNAi into RISC. Dicer-substrate RNAi molecules are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional RNAi molecules. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs.

"Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (e.g., about 35 nucleotides upstream and about 40 nucleotides downstream) arise from restriction enzyme sites within the multiple cloning site of the RNAi. As used herein the term "miRNA" encompasses both the naturally occurring miRNA sequences as well as artificially generated miRNA shuttle vectors.

The RNAi can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

The present disclosure contemplates the use of any genetic manipulation for use in modulating the expression of EZH2 and/or YY1. Examples of genetic manipulation include, but are not limited to, gene knockout (e.g., removing the EZH2 and/or YY1 gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Exemplary methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present disclosure, vectors are administered into tumors or tissue associated with tumors using direct injection. In other embodiments, administration is via the blood or lymphatic circulation (See e.g., PCT publication 1999/02685 herein incorporated by reference in its entirety). Exemplary dose levels of adenoviral vector are preferably $10^8$ to $10^{11}$ vector particles added to the perfusate.

In some embodiments, the present disclosure provides antibodies that inhibit EZH2 and/or YY1. Any suitable antibody (e.g., monoclonal, polyclonal, or synthetic) may be utilized in the therapeutic methods disclosed herein. In some embodiments, the antibodies are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, candidate EZH2 and/or YY1 inhibitors are screened for activity (e.g., using the methods described herein or another suitable assay).

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

II. Methods of Preventing or Reversing T Cell Exhaustion

Provided herein are methods of reversing or preventing T cell exhaustion through inhibition of EZH2 and/or YY1. In some embodiments, reversing or preventing T cell exhaustion finds use in the treatment of cancers such as immune responsive cancers such as, e.g., ovarian cancer (Preston et al., 2011), melanoma (Boon et al., 2006), non-small lung cancer (Anagnostou and Brahmer, 2015), neuroblastoma (Yu et al., 2010), synovial sarcoma (Robbins et al., 2015) and other cancers; or chronic infectious disease (e.g., chronic viral diseases such as, e.g., HIV (Porichis and Kaufmann, 2011; Zhang et al., 2007), HCV, CMV, EBV or HBV (Ha et al., 2008a; Ha et al., 2008b; Peng et al., 2008; Protzer et al., 2012; Wherry, 2011), or chronic infections with intracellular organisms (e.g., *M. leprae, Leishmania*).

In some embodiments, EZH2 and/or YY1 inhibition is utilized in ex vivo methods (e.g., cancer immunotherapy methods). For example, in some embodiments, T cells (e.g., YY1 and/or EZH2 inhibitor) from a patient (e.g., patient diagnosed with cancer or chronic infectious disease) are removed from peripheral blood, hepatocytes in case of chronic HIV (Porichis et al., 2011; Zhang et al., 2007) or HCV or HBV infections (Peng et al., 2008; Protzer et al., 2012) or Peripheral blood and tumors (in case of cancers), expanded, treated with EZH2 and/or YY1 inhibitors (e.g., siRNA) or supplied with an expression system (e.g., vector) that reduces or knocks out expression of EZH2 and/or YY1 and then re-introduced into the patient. In some embodiments, T cell are further engineered ex vivo to make them suitable for immunotherapy (e.g., activation or introduction to tumor or viral antigens).

In some embodiments, T cells are Chimeric Antigen Receptor (CAR) T cells. CARs are engineered receptors, which graft an arbitrary specificity onto an immune effector cell. Typically, these receptors are used to graft the specificity of a monoclonal antibody onto a T cell; with transfer of their coding sequence facilitated by retroviral vectors. The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. When T cells express this molecule (usually achieved by oncoretroviral vector transduction), they recognize and kill target cells that express the target (e.g. cancer cells).

In some embodiments, the variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal. In some embodiments, the CAR T cells have had the YY1 and/or EZH2 genes knocked out (e.g., using CRISPR/CAS9, recombination, or other suitable methods).

In some embodiments, CRISPR/Cas9 systems are used to delete or knock out genes. Clustered regularly interspaced short palindromic repeats (CRISPR) are segments of prokaryotic DNA containing short, repetitive base sequences. These play a key role in a bacterial defense system, and form the basis of a genome editing technology known as CRISPR/Cas9 that allows permanent modification of genes within organisms.

In some embodiments, vectors used to make CAR T cells (e.g., retrovectors) also include nucleic acids that encode recombinant EZH2 and/or YY1 inhibitors (e.g., antisense oligonucleotides). In some embodiments, nucleic acids encoding antisense agents are under the control of an inducible promoter.

CARs can be made against any cancer antigen and there can be several different designs to develop CARs with YY1 or Ezh2 inactivation. A prototypical design of CAR is described here: To produce a CAR vector, a single chain variable region (scFv) of tumor antigen binding regions of both heavy and light chains of a monoclonal antibody, a hinge, a transmembrane domain and an endodomain with a signaling domain derived from CD3-ζ. CARs can incorporate CD28 costimulatory molecule as a transdomain in a second generation CAR or as an endodomain co-stimulatory signaling along with other costimulatory endodomains in third generation CARs. The CAR vector design incorporates RNAi to YY1, EZH2, or pathway components (Dotti et al., 2014; Hudecek et al., 2013; Ma et al., 2002; Sadelain et al., 2013)

In the context of T-cell mediated therapies, the number of T-cell administered to a subject in need thereof is dependent on the specific disease and type of treatment. In some embodiments, $10^7$ to $10^{11}$ modified T-cells are administered.

In some embodiments, prior to or during treatment with an EZH2 and/or YY1 inhibitor, a sample from the patient (e.g., T cell sample from peripheral blood or a tumor or cancer sample) is assayed for expression or overexpression of EZH2 and/or YY1. In some embodiments, only patients with T cells that express or overexpress EZH2 and/or YY1 are administered anti-EZH2 and/or YY1 treatments. In some embodiments, the expression and/or overexpression of EZH2 and/or YY1 is to a level above the expression in a T-cell from a patient that does not have disease and/or T-cell exhaustion. In some embodiments, the level of expression is greater than that in a T-cell sample from the same subject from an area not associated with disease (e.g., skin). In some embodiments, during or after treatment, samples are re-tested to determine if the EZH2 and/or YY1 inhibitors have reduced the expression levels of EZH2 and/or YY1. In some embodiments, the level of expression of EZH2 and/or YY1 before, during, or after treatment with an EZH2 and/or YY1 inhibitor is used to determine a treatment course of action (e.g., administration of EZH2 and/or YY1 inhibitor, dose or timing of EZH2 and/or YY1 inhibitor, or selection of an alternative treatment).

In some embodiments, once a cancer or infectious disease is known to be one associated with T-cell exhaustion, no testing for T-cell exhaustion is performed prior treatment.

In some embodiments, ex vivo T cells treated with EZH2 and/or YY1 inhibitors are administered to a subject in combination with a EZH2 and/or YY1 inhibitor.

In some embodiments, the compounds and pharmaceutical compositions described herein are administered in combination with one or more additional agents, treatment, or interventions (e.g., agents, treatments, or interventions useful in the treatment of cancer).

In some embodiments, EZH2 and/or YY1 inhibitors are co-administered with an anti-cancer agent (e.g., chemotherapeutic) or anti-viral agent. In some embodiments, method embodiments of the present disclosure encompass co-administration of an anti-cancer agent (e.g., chemotherapeutic) and/or an anti-checkpoint receptor agent (e.g., nivolumab). The present disclosure is not limited by type of anti-cancer agent co-administered.

In some embodiments, the therapies described herein are used in combination with other immunotherapies (e.g., CAR-T/TCR, antibody immunotherapy, and/or checkpoint receptor inhibitors).

Experimental

The following examples are provided in order to demonstrate and further illustrate certain preferred embodiments and aspects of the present disclosure and are not to be construed as limiting the scope thereof.

Experimental Methods

Tissue and Blood Samples

Studies involving de-identified human samples were obtained after approval through the Tufts Health Science Campus Institutional Review Board (IRB). The malignant melanoma and normal healthy skin frozen sections were obtained from the Cooperative Human Tissue network (Philadelphia, Pa.). The purified peripheral blood mononuclear cells (PBMCs) from untreated ten HIV patients were obtained upon request from Retrovirus laboratory, University of Washington, Seattle, Wash. Universal precautions were followed while working with the human samples.

Bioinformatics

The IL2 promoter (GenBank and promoter database accession number, NM_000586 and 32233, respectively) and YY1 promoter (GenBank and promoter database accession number, NM_003403 and 12193, respectively) were retrieved using the transcriptional regulatory element database (TRED). The data on transcription factors binding to the consensus binding sequences were obtained through TRANSFAC database). The "best selection criteria" was used for transcription factor binding sites to help minimize false positives.

Reporter Plasmids, Reporter Assays and Site Directed Mutagenesis

A human IL2 promoter luciferase pGL3-NFAT plasmid (−326 to +46 bp) was a gift from Jerry Crabtree (Addgene plasmid #17870) (Clipstone and Crabtree, 1992 Nature 357, 695-697; Northrop et al., 1994 Nature 369, 497-502). The YY1 binding site, 5'-CCCCCATAAT-3', (SEQ ID NO: 38) in the IL2 promoter luciferase was mutated to 5'-aaCaaAgAAc-3'(SEQ ID NO: 39) using the service of GenScript Inc. (item cat. SC1622). Human YY1 promoter luciferase construct YY1-pGLuc-basic was a kind gift from Dr. Guangchao Sui of Wake Forest Health Sciences, NC (Huang et al., 2012 Nucleic Acids Res 40, 1033-1049). The cJun/ATF2 octameric palindrome cyclic AMP-response element (CRE), 5'-TGACGTCA-3'(SEQ ID NO: 40), was mutated to 5'-cGgCaTaA-3' (SEQ ID NO: 41) using the service of GenScript Inc. (Item cat. 426354-1).

The reporter assays and plasmid overexpression were performed in 6 well tissue culture plates. $5 \times 10^6$ T cells were transfected with plasmids using Amaxa human T cell nucleofector Kit, cat. VPA-1002 (Lonza). Transfections were performed using Amaxa nucleofector II device, program no. T-023/T-020. Luciferase assays were generally performed 48 hours after transfections. The IL2 promoter construct was ectopically expressed the in combination with a renilla lucifearse reporter to serve as an internal control and activity was measured using dual luciferase reporter assay system (Promega, cat. E1910). The YY1 promoter luciferase assay was measured from T cell culture supernatants using BioLux Gaussia lucferase assay kit (New England Biolabs, cat. no. E3300S). Amounts of transfected plasmids were kept proportionally constant. Samples were assayed for reporter activity using a Gloma 20/20 Luminometer (Promega), essentially using the recommended parameters provided by the reagent suppliers.

Antibodies, shRNA and Inhibitors

The following antibodies were used for cell staining: PE-conjugated anti-human CD279 (PD-1) (cat. 12-2799), CD223 (LAG-3) (cat. 12-2239), Tim3 (cat. 12-3109), and CD3-PECyanine7 (cat. 25003182), all of which were purchased from eBioscience, and FITC-conjugated anti-human CD8 (Invitrogen) and CD4 (BD Biosciences, cat. 340133). Pacific Blue-conjugated PD1 (cat. 329920), PE-conjugated PD-L1 (cat. 329705) and purified PD-L1 (cat. 329702) was purchased from BioLegend. In addition, PE-conjugated (cat. 555783, Pharmingen) was used as an isotype control. T cell apoptosis was detected through flow cytometric analysis using the FITC Annexin V apoptosis detection kit I (BD Pharmingen, cat. 556547) in conjunction with the vital dye, propidium iodide (BD Pharmingen, cat. 51-66211E). In addition, following antibodies were used in westerns, phospho-MKK3$^{(Ser189)}$/MKK6$^{(Ser207)}$ (cat. 12280), phospho-SEK1/MKK4$^{(Ser257/Thr261)}$ (cat. 9156), MKK3 (cat. 5674), SEK1/MKK4 (cat. 9152BC), p38-alpha MAPK (cat. 9217BC), phospho-p38 MAPK$^{(T180/Y182)}$ (cat. 4511BC), ZAP-70 (cat. 2709BC), phospho-ZAP-70$^{(Y319)}$/Syk$^{(Y352)}$ (cat. 2701BC), AKT (cat. 9272), phospho-AKT$^{(S473)}$ (cat. 9271), p44/42 MAPK (Erk1/2) (cat. 9102), phospho-p44/42 MAPK (Erk1/2)$^{(Thr202/Tyr204)}$ (cat. 9106) and β-actin (cat. 4970S), all of which were purchased from Cell Signaling, and anti-Ezh2 (cat. 07-689), anti-YY1 (cat. AB10007), anti-phospho-ATF2$^{(Thr69/71)}$ (cat. 05-891) and anti-ATF2 (cat. 04-1021), all of which were purchased from Millipore. Anti-cJun (BD, cat. 610326) and phospho-c-Jun$^{(Ser63/73)}$ antibodies (Santa Cruz, cat. sc16312) were also used. The human IL2 neutralizing antibody was purchased from R & D Systems (cat. AF-202-NA). An anti-p38α MAP Kinase$^{(Tyr-323)}$ (cat. PP3411) was acquired from ECM Biosciences. The human YY1 specific shRNA (cat. sc-36863) and control shRNA plasmid (sc-108060) were obtained from SantaCruz Biotechnology.

Figure 18:
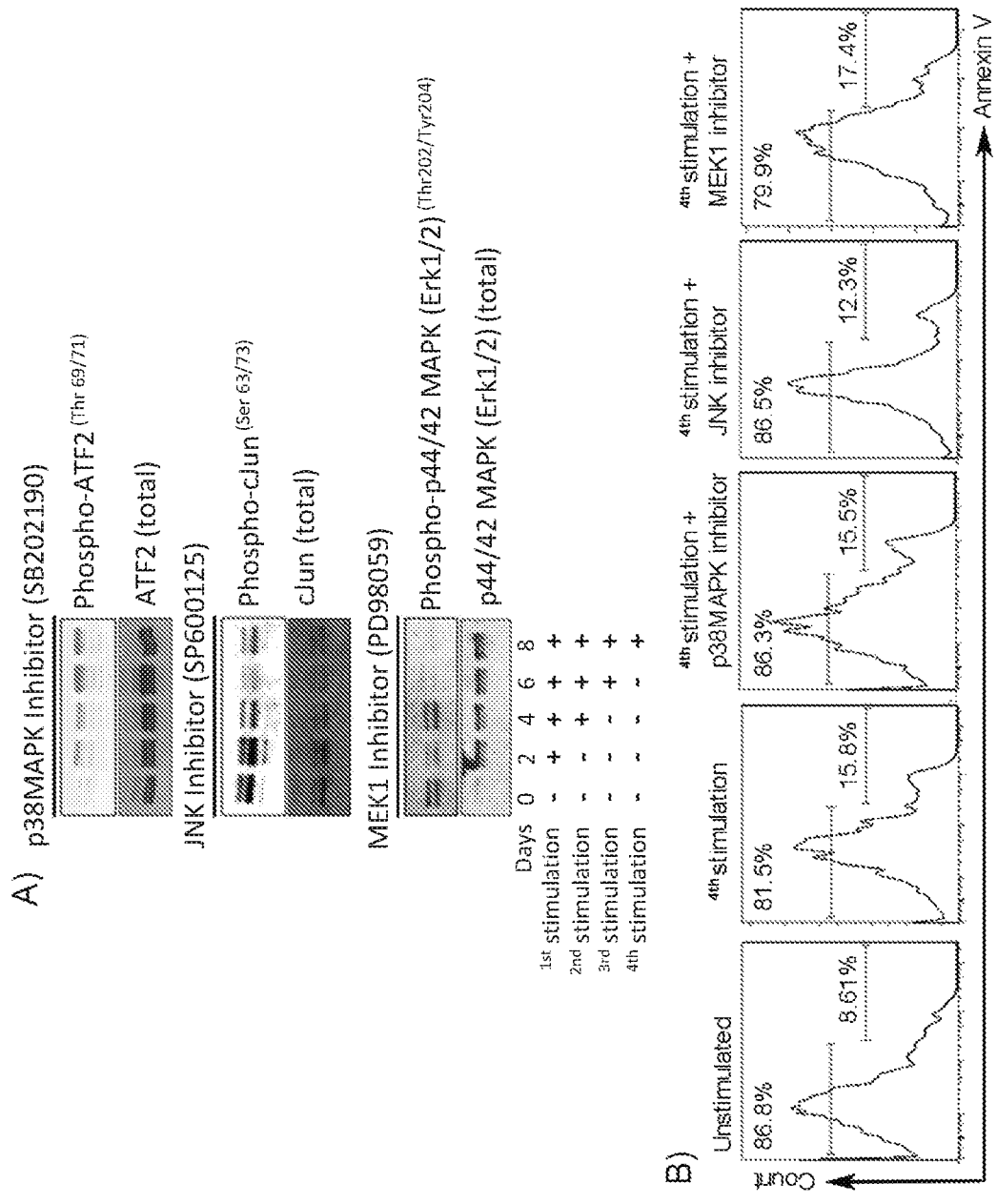
FIG. 18 shows targeted inhibition of p38MAPK/JNK signaling pathways. (A) Kinase activities by western blot. (B) Viability by Annexin V staining. As a control on nonspecific toxicity, CD8+ T cells in (A) were stained with Annexin V after the $4^{th}$ stimulation and analyzed by FACS for cellular apoptosis. Viability of >80% was maintained in all cultures.

In experiments using p38MAPK, JNK, MEK1 and Ezh2 inhibitors, cells were grown in the continued presence of inhibitors. After each wash and activation step, cells were treated with a fresh batch of inhibitors. The following inhibitors were used: MAPKp38-SB202190 (10 µmol/ml) (Sigma, cat. S7067), JNK-SP600125 (10 µmol/ml) (Sigma, cat. S5567), MEK1-PD98059 (5 µmol/ml) (Calbiochem, cat. 513001), MEK1/2-inhibitor III (5 µmol/ml) (Calbiochem, cat. 444966) and Ezh2-UNC999 (10 nmol) (Millipore, cat. 505052). DMSO was used as a mock treatment. The specificity of p38MAPK, JNK and MEK1 inhibitors to block the downstream kinases, phospho-ATF2, phospho-cJun and phospho-ERK, respectively, was confirmed by westerns (FIG. 18A). The continued presence of p38MAPK/JNK/MEK1 inhibitors in T cell culture did not produce noticeable toxicity (FIG. 18B).

Westerns, Native Gels and Co-Immunoprecipitations

For denaturing westerns, 20-40 µg of protein extracted from T cells was used. RIPA lysis buffer (Sigma, cat. R0278) was used to prepare whole cell extracts. For native gel analysis, cells were lysed in native lysis buffer (50 mM Tris-Cl, pH 8.0; 1% NP40; 150 mM NaCl, 100 µg leupeptin, 1 mM PMSF, 5 mM orthovanadate). For both native and denaturating conditions, samples were resolved on 4-15% TGX precast gels (Bio-Rad, cat. 456-1084) with the difference in running buffer. Native samples were run without SDS. Generally, 10 µg of protein extract dissolved in 2× Native PAGE sample buffer (Bio-Rad, cat. 161-0738) was run on the gel following the standard procedures described previously (Balkhi et al., 2010 Cell Signal 22, 117-127). For Co-IPs, CD8 enriched T cells were stimulated repeatedly in vitro and lysed in a standard Co-IP lysis buffer, and then 500 µg of whole cell extract was prepared and incubated with YY1 antibody pre-absorbed to Protein A/G Agarose (Santa Cruz Biotechnology, cat. sc-2003). Western transfers were performed on Immobilon transfer membranes (Millipore, cat. IPVH08100). Membranes were blocked for 1 hr at RT in TBS-T buffer containing 5% dry skim milk powder and then incubated overnight in primary antibody. Membranes were washed 3 times in TBST-milk and incubated for 1 hr in anti-mouse or anti-rabbit IgG-HRP antibodies (GE Healthcare, cat. NA931 and NA934). After secondary antibody incubation, membranes were thoroughly washed for 2 hours. Immuno-detection was performed using chemiluminescence substrate reagents (Perkin Elmer) and autoradiography detection on HyBlot CL film (Denville Scientific). Membrane stripping was performed with Restore Western blot stripping buffer (Thermo Fisher Scientific, cat. 21059). The immunoprecipitation and westerns were performed with antibodies derived from different species to avoid cross reactivity.

Chromatin Immunoprecipitation and Electrophoretic Mobility Shift Assay (EMSA)

Chromatin immunoprecipitation assay. The ChIP assay was performed using a ChIP-IT high sensitivity kit (Active Motif, cat. 53040), following the manufacturer's recommended protocol. Human CD4+ T cells were repeatedly activated with CD3/CD28 beads in the continued presence of Ezh2 inhibitor or transfected with YY1 shRNA and a control after 2$^{nd}$ stimulation. Approximately 15 µg of chromatin was used in each reaction with an antibody that specifically recognizes H3K27me3 (Active Motif, cat. 39155). Fold enrichment was calculated relative to IgG and input. The primer pair that amplifies the IL2 promoter sequence containing the YY1 binding site: F-5'-CATCAGAAGAGGAAAAATGAAGGT-3' (SEQ ID NO: 42), R-5'-TCTTGAACAAGAGATGCAATTTAT-3' (SEQ ID NO: 43) was used.

EMSA was performed using LightShift chemiluminescent EMSA kit (Thermo Scientific, cat. 20148). The manufacturer's procedure was followed to perform the assay. The primer duplex containing the cJun/ATF2 octameric palindrome cyclic AMP-response element (CRE) present on the YY1 promoter was modified with biotin at the 5' end. The following primer duplex:

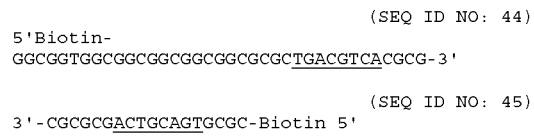

was used.

In addition, a non-specific biotin modified probe provided by the manufacturer was used. Ten µg of nuclear extract obtained from the activated T cells was used in the binding reaction. All the reaction components, phospho-cJun and ATF2 were added in the order recommended by the manufacturer. Gels were run in 0.5× TBE using 4-15% precast polyacrylamide gels, subsequently gels were transferred onto a positively charged nylon membrane (Hybond-N+, Amersham pharmacia biotech) in 0.5× TBE. The transfer membrane was crosslinked for 10-15 minutes using UV transilluminator (Fisher Scientific). Protein binding to the biotin-labeled DNA was detected through chemiluminescence method as described by the manufacturer. To detect phospho-cJun and phospho-ATF2 binding to the probe, the membrane was first incubated with secondary rabbit HRP antibody. The same membrane was stripped and reprobed with secondary mouse HRP. DNA oligonucleotides were acquired from Sigma. Each time EMSA was performed, a complete set of three control reactions provided by the supplier was used.

Immunohistochemistry and Immunofluorescence

Formalin-fixed paraffin tissue samples of human metastatic melanoma were cut at 4 µm sections and placed on positively-charged slides. Slides were subsequently incubated in a 60° C. oven for 1 hour, cooled, and deparaffinized. Rehydration of slides was performed in graded ethanol solutions. Antigen retrieval was performed by the Heat-Induced Epitope Retrieval procedure. In this procedure slides were first placed in a IX solution of Target Retrieval Solution (Dako, pH 6) for 25 min at 96° C. using a vegetable steamer (Black and Decker) and cooled for 20 min. Endogenous peroxidase was blocked by incubating the slides in 3% hydrogen peroxide aqueous solution and 10% goat serum. Sections were then sequentially stained, first with mouse anti-CD3 (Santa Cruz, sc-1239) for 60 min. then with HRP goat anti-mouse polymer secondary antibody (Vector) for 30 min. The chromogen used was 3,3'-diaminobenzidine (DAB+, Vector Labs). Rabbit anti-YY1 (Abcam, cat. ab109237) and rabbit anti-Ezh2 (Novus Biological, cat. NBP2-38143) was subsequently applied, followed by secondary biotinyated goat anti-rabbit. ABC alkaline phosphatase was used for the YY1 and Vector Red was a chromogen. A negative control consisted of omitting the primary antibody.

For IF, the fresh-frozen mounted sections were fixed with methanol at −20° C. for 5 min. Sections were permeabilized with 0.25% Triton-X-100 for 20 min, and then blocked with 2% normal horse serum in PBS for 20 min. Sections were incubated overnight in a cocktail of primary antisera of CD3/PD1 and CD3/phospho-cJun for dual immunofluorescence. The primary antibodies used were mouse anti-PD1 (cat. ab52587), goat anti-CD3 (Santa Cruz, cat. sc-1127), and rabbit ant-phospho-cJun$^{(Ser63/73)}$ (Santa Cruz, cat. sc-16312-R). Subsequent detections were performed with a mixture of secondary antibodies consisting of Cy3-conjugated donkey anti-rabbit IgG (Jackson Immunoresearch, 1:200), Alexa 488-conjugated donkey anti-mouse IgG (Jackson), and Cy3-conjugated donkey anti-sheep IgG (Jackson). Images were captured with a Carl Zeiss Axioskop fluorescence microscope (Axioskop 40; Carl Zeiss Inc.)

qRT-PCR and ELISA

Total RNA was extracted from T cells using Trizol Reagent (Life Technologies). Reverse transcription reactions were performed using M-MuLV reverse transcriptase (New England Biolabs, cat. M0253L). qPCR amplification reactions were performed using SYBR GREEN PCR master mix (applied biosystems). The following primers were used in the qPCR amplification reactions: IL2, F-5'-AACTCCTGTCTTGCATTGCAC-3' (SEQ ID NO: 46), R-5'- GCTCCAGTTGTAGCTGTGTTT-3'(SEQ ID NO: 47); IFNγ, F-5'-TCGGTAACTGACTTGAATGTCCA-3' (SEQ ID NO: 48), R-5'-TCGCTTCCCTGTTTTAGCTGC-3' (SEQ ID NO: 49); YY1, F-5'-ACGGCTTCGAGGATCA-GATTC-3' (SEQ ID NO: 50), R-5'-TGACCAGCGTTTGTTCAATGT-3'(SEQ ID NO: 51); GAPDH, F-5'-ACAACTTTGGTATCGTGGAAGG-3'(SEQ ID NO: 52), R-5'-GCCATCACGCCACAGTTTC-3' (SEQ ID NO: 53) Gene amplification reactions were performed with iCycler 480 (Roche). Fold changes were calculated using the LightCycler software basic relative quantitation method (ΔΔcp). ΔΔcp$_{(Fold\ Change)}$=Δcp Target$_{(Gene)}$−Δcp Calibrator$_{(GAPDH)}$.

ELISA assays were performed using human IL2 and IFNγ Ready-SET-Go kits (eBioscience). Three replicates were included for each experimental set and each experiment was repeated three or more times. ELISA was performed on the supernatant saved from each stimulation step. CD4+ or CD8+ T cells were stimulated with anti-CD3/CD28 beads and cultured for 48 hours, after which cells were spun down and supernatants carefully removed and saved at −20° C. The same procedure was followed for the rest of the stimulation steps.

Cell Culture and Flow Cytometry

Human T cell isolation and culture in vitro. CD4+ and CD8+ T cells were enriched from peripheral blood mononuclear cells obtained from healthy donors. Leukoreduction filters from Boston Children's Hospital that were processed using histopaque (Sigma) cushions to separate PBMCs were used. Human CD8+ and CD4+ cells were enriched using naïve CD8 and CD4 T cell enrichment cocktail (BD Biosciences, cat. 51-900481 and 9002314, respectively). Approximately 1×10$^6$ T cells were initially plated in 24 well plates suspended in AIM-V medium (Life Technologies, cat. 12055-083), 5% heat inactivated human serum (Sigma, cat. F4135) without IL2 unless stated. IL2 when included in the growth medium was used at concentration of 300 IU/ml (Chiron). Cells were stimulated the same day with T-Activator CD3/CD28 dynabeads (Life Technologies, cat. 11131D) following the manufacturer's recommendations. 48 hours after the first stimulation, cells were counted and washed, and beads were removed using a magnet. This was followed by a second, third and fourth round of stimulations with fresh batches of CD3/CD28 beads. In each stimulation step, the amount of beads used and the number of viable cells activated were kept proportionally equal. In the experiments requiring selective activations with anti-CD3 or anti-CD28 antibody alone, immobilized anti-OKT3 or anti-CD28 antibodies at a concentration of 1 µg/ml were used.

Intracellular staining of T cells for flow cytometry analysis was performed using intracellular fixation and permeabilization buffer set (eBioscience, cat. 88882400). Briefly, T cells were incubated first with fluorescent conjugated surface antibodies for 40 minutes in FACS buffer. This followed a onetime wash. Cells were then fixed with 100 µl fixation buffer for 30 minutes followed by washes to remove fixation buffer. After the washes, cells were incubated for additional 30 minutes in 1× permeabilization buffer containing either anti-YY1 (Alexa 488) (abcam, cat. 199814) or anti-Ezh2 (Alexa 647) (BD Biosciences, cat. 563491), followed by two time washes in permeabilization buffer before flow cytometry analysis.

Flow cytometry of stained PBMCs and cultured T cells was performed with a multicolor BD LSR II at the Tufts University School of Medicine flow cytometry core. Analyses were performed with Flow Jo software. Samples with intracellular staining were gated on the well-permeabilized fraction.

CEA-CAR T Cells and Retroviral Transduction

To produce second generation CEA-CAR T cells, T cells were modified by retroviral gene therapy to express a single chain antibody domain (sFv) that recognizes CEA tumor antigen. This anti-CEA binding domain is fused together with the full length sequence of CD28 co-stimulatory molecule and sequences of the signaling chain of the CD3 complex (signal 1+2) (FIG. 6A) (Nolan et al., 1999). The clinical grade CEA-CAR vector producing cells have been successfully tested in a number of in vitro studies as well as in a clinical setting to modify T cells for breast cancer clinical trials (Katz et al., 2015). The first generation CEA-CAR contains anti-CEA binding domain fused with signaling chain (signal 1) (Nolan et al., 1999 Clin Cancer Res 5, 3928-3941). Transduction of T cells with anti CEA-CAR vector were as previously described (Beaudoin et al., 2008 Nat Med 9, 540-547).

MIP101 and MIPCEA, tumor cell coculture with CEA-CAR modified T cells. MIP101 is a CEA-undifferentiated human carcinoma cell line derived from liver metastases of colonic adenocarcinoma patients. The MIPCEA cell line was generated by stably expressing the full length CEA gene in MIP101 cells (Thomas et al., 1995 Cancer Lett 92, 59-66). All cell lines tested negative for mycoplasma contamination using mycoplasma detection kit (Sigma, cat. D9307). Their coculture with CAR-T cells was performed in 12 well tissue culture plates. Approximately $3 \times 10^5$ tumor cells were plated overnight prior to coculture. The next day, cells were treated with Mitomycin C (Millipore, cat. 475820) for 1 hr, following which cells were carefully washed three times. This was followed by their coculture with CAR-T cells in a 1:1 ratio either in the absence or presence of 10 nm Ezh2 inhibitor (Millipore, cat. 505052) (Konze et al., 2013 ACS Chem Biol 8, 1324-1334). Ezh2 inhibitor treatment was performed by incubating CAR-T cells with the inhibitor for 1 hour, after which CAR-T cells were put in coculture with the tumor cells. After 48 hours of coculture, CAR-T cells were recovered from culture, washed and exposed to a second batch of Mitomycin C treated tumor cells either in the absence or presence of 10 nm Ezh2 inhibitor for an additional 48 hours. Modified T cells were again recovered, washed and exposed to a third batch of Mitomycin C treated tumor cells either in the absence or presence 10 nm Ezh2 inhibitor for an additional 48 hours. Each time after the coculture, tumor cells were trypsinized (cellgro) and counted. In experiments requiring blocking of PD1 (nivolumab) or PD-L1 in MIP-CEA and MIP101 cells, 20 µg and 5 µg respectively of clinical grade anti-PD1 antibody (courtesy Tufts Medical Center, Department of transfusion medicine) and purified anti-PD-L1 antibody (cat. 329702) were used.

Statistical Analysis

Data are presented as averages±SD. Student's t-test was applied to perform pair-wise comparisons between different treatment groups or between control and treatment groups. P values less than 0.05 were considered statistically significant.

Results

In Vitro Exhaustion Model

Figure 9:
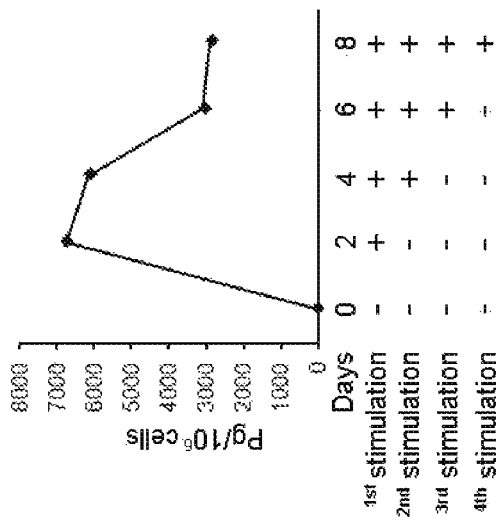
FIG. 9 shows that IFNγ production declines after repeated stimulations. ELISA for IFNγ production in CD4 T cells repeatedly stimulated in the presence of IL2.
Figure 10:
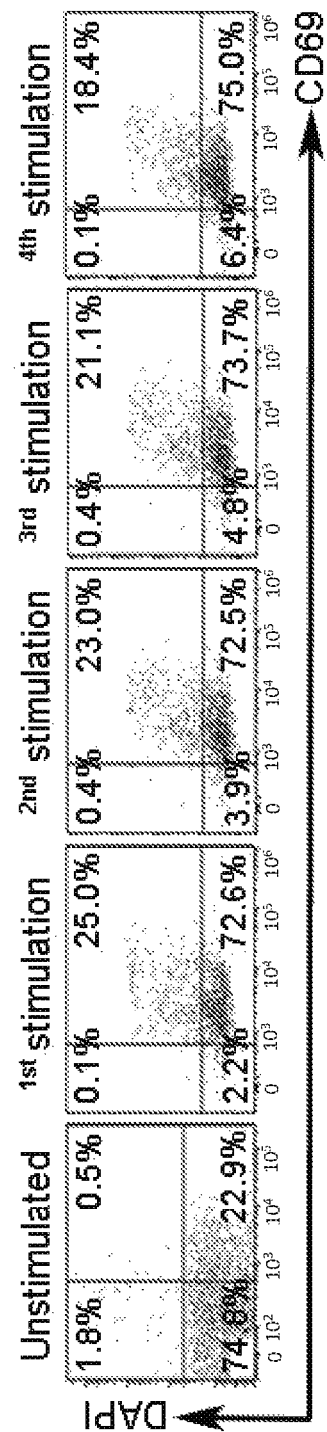
FIG. 10 shows that exhausted T cells maintain activation status and viability after repeat stimulation.
Figure 11:
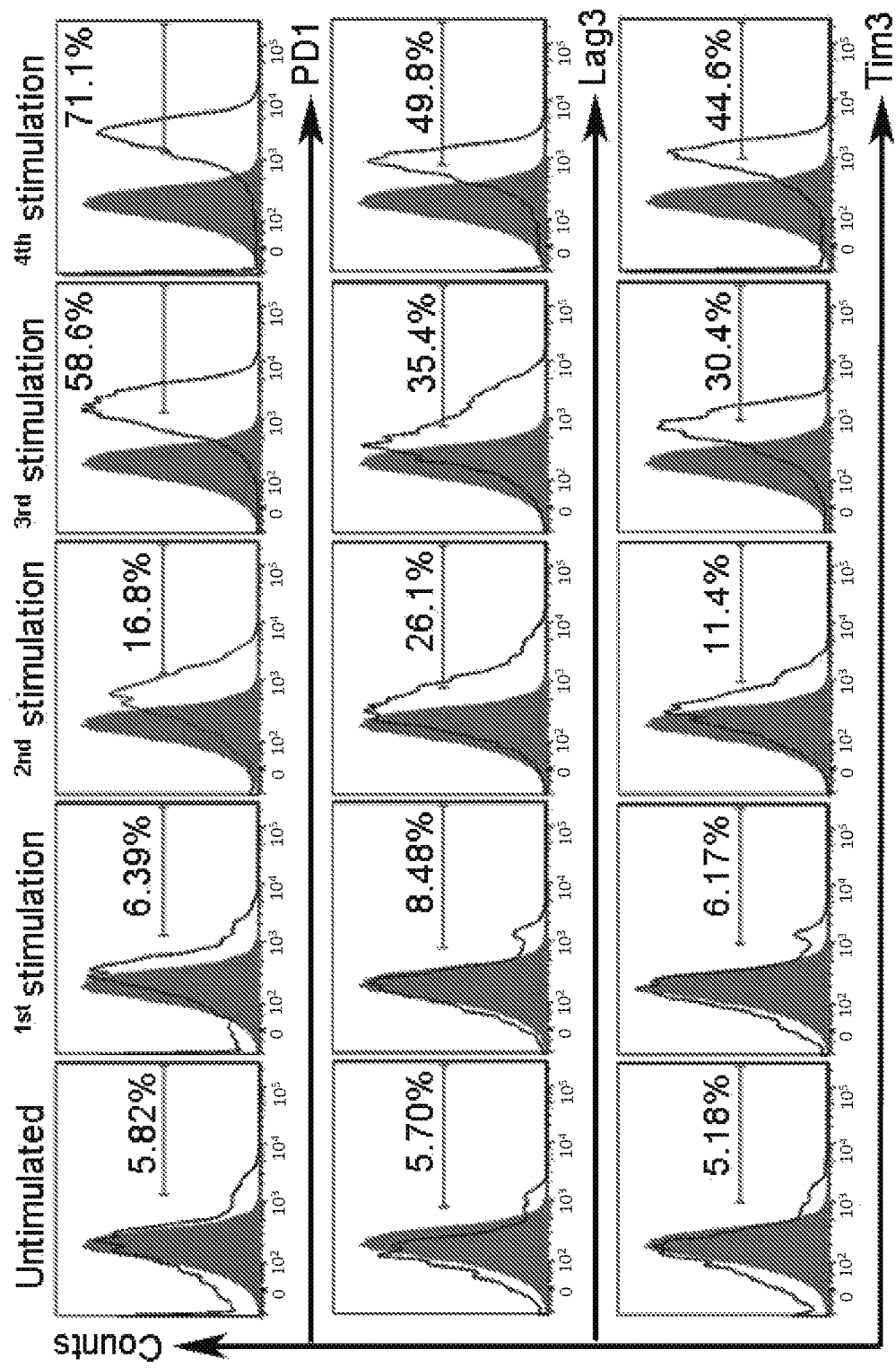
FIG. 11 shows that IL2 supplementation does not block exhaustion marker progression.
Figure 12:
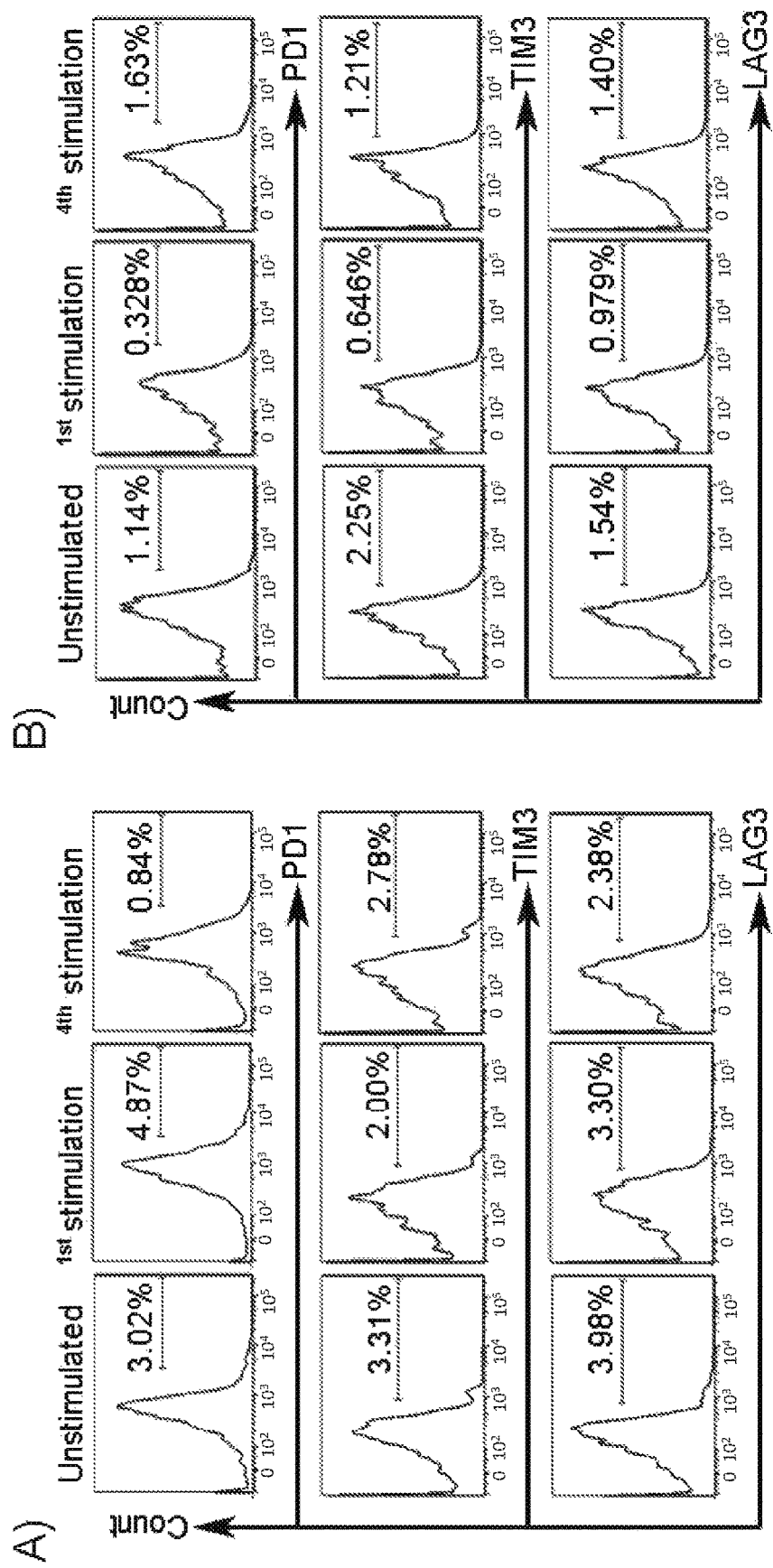
FIG. 12 shows that persistent activation of T cells with signal 1 or signal 2 alone does not induce exhaustion phenotype. (A-B) FACS for exhaustion markers after repeat stimulation of CD4 T cells with immobilized (A) anti-CD3 or (B) anti-CD28 antibody on tissue culture plates.

Exhaustion is an in vivo defined phenomenon. To study exhaustion experimentally, an in vitro system to recapitulate the process was used. Building on prior observations (Emtage et al., 2008 Clin Cancer Res 14, 8112-8122), a procedure was established where normal resting human T cells were continuously exposed to signal 1+2 with anti-CD3/CD28 beads, repeated at 2-day intervals, which was previously shown to stimulate then lose production of IL2 (FIG. 1A). This pattern of cytokine failure was confirmed in the current model for IL2 and IFNγ both (FIG. 1B and FIG. 9). Upon repeated stimulation, CD4 and CD8 T cells also expressed markers of exhaustion, namely checkpoint receptors PD1, Tim3 and Lag3, that shifted progressively higher with each stimulation (FIG. 1C). The cells maintained viability during these stimulations and sustained CD69 expression, a marker of T cell activation (FIG. 10). Marker progression was independent of IL2 depletion as the same results were obtained with 330 IU/ml of exogenously supplemented IL2 (FIG. 11). Lastly, repeated stimulation of T cells with immobilized anti-CD3 or anti-CD28 antibody alone was insufficient to induce exhaustion (FIG. 12A, B), confirming a key distinction from other processes such as anergy in which isolated Signal 1 is effective (Appleman and Boussiotis, 2003 Immunol Rev 192, 161-180; Balkhi et al., 2015, supra). Taken together, this in vitro model mimics in vivo persistent stimulation of T cells entering into an antigen-rich environment and successfully recapitulates key features of the exhaustion phenotype.

YY1 Recruits Ezh2 to Repress IL2

The IL2 secretion pattern was paralleled in mRNA levels, starting high following activation and then declining (FIG. 1D), and was also reflected in reporter assays using an IL2 promoter construct in recurrently stimulated T cells (FIG. 1E). To identify putative sites for transcription factor binding that could regulate IL2 transcription during exhaustion, an in silico analysis of the IL2 promoter was performed by searching the Transfac database (Biobase). Several sites identified with high confidence were associated with transcriptional activation (FIG. 13). In contrast, the presence of a single YY1 binding site attracted interest due to its known potential for negative as well as positive regulation. This site was in close proximity to sites for the high mobility group protein 1 (HMG1) and TATA binding protein, marking YY1 as a strong candidate for IL2 gene repression.

Yin Yang 1 (YY1) is a ubiquitous and multifunctional zinc-finger transcription factor that regulates diverse cellular functions, including B cell development, proliferation, differentiation and tumorigenesis (Gordon et al., 2006 Oncogene 25, 1125-1142; Liu et al., 2007 Genes Dev 21, 1179-1189). YY1 regulates both positively and negatively (whence the name yin-yang) after binding to the consensus sequence 5'-CCGCCATNTT-3' (SEQ ID NO: 37) in the promoters of these genes (Thomas and Seto, 1999, supra). As a member of the polycomb group (PcG) proteins, YY1 may recruit and cooperate with other members of the complex that function as chromatin modifiers (Atchison, 2014 Front Immunol 5, 45; Shi et al., 1997 Biochim Biophys Acta 1332, F49-66; Srinivasan and Atchison, 2004 Genes Dev 18, 2596-2601; Woo et al., 2013 Mol Cell Biol 33, 3274-3285). Enhancer of zeste homolog 2 (Ezh2) is a component of the Polycomb Repressor Complex 2 (PRC2), one of two classes of PcG, and possesses histone H3-K27 trimethylation (HKMT) activity that can directly impede gene transcription (Caretti et al., 2004, supra).

Figure 14:
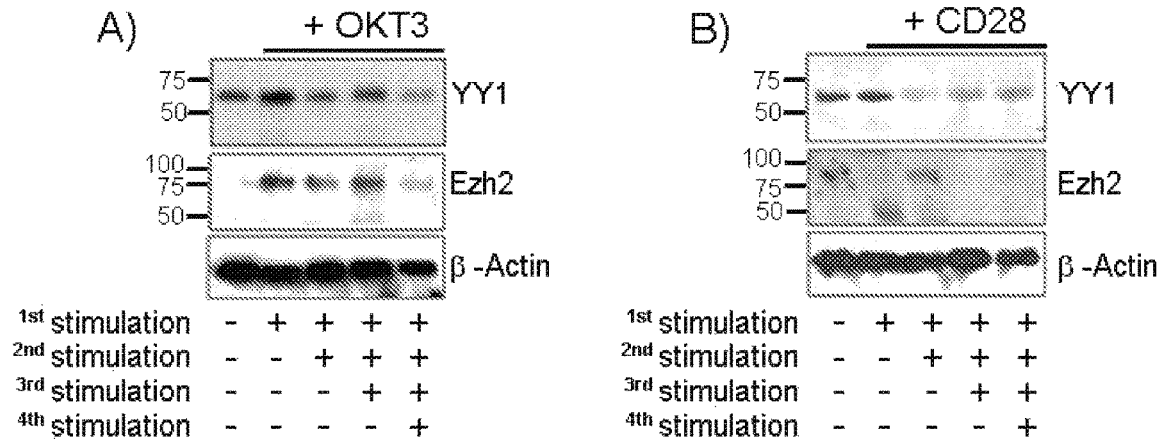
FIG. 14 shows that persistent activation of T cells with signal 1 or signal 2 alone does not increase YY1 or Ezh2. Western blot of YY1 and Ezh2 protein in CD4 T cells that were repeatedly stimulated with immobilized (A) anti-CD3 antibody or (B) anti-CD28 antibody. β-actin was loading control.

Western blotting confirmed marked increases in YY1 and Ezh2 protein with repeated stimulations in enriched CD4 (FIG. 2A) and CD8 T cells. In contrast, the response from single stimulations did not recapitulate the pattern of protein increases over time, confirming the necessity of repeat stimulations for active product accumulation (FIG. 2B; compare day 8 signals for 1-4 stimulations). Immunofluorescence confirmed high levels of YY1 and Ezh2 in repeatedly stimulated T cells compared with resting T cells (FIG. 2C). No increase in expression of YY1 or Ezh2 was observed when T cells were repeatedly stimulated with immobilized anti-CD3 or anti-CD28 antibody alone (FIG. 14A, B), confirming the necessity of two signals for these two nuclear proteins' expression as also noted for the classical surface exhaustion markers above (FIG. 1C).

If H3-K27 trimethylation and IL2 failure result from cooperation of YY1 and Ezh2 during exhaustion, it follows that blocking YY1 or Ezh2 should be equally preventative. To examine this possibility, a small molecule Ezh2 inhibitor was maintained in the activation cultures or T cells were transduced with short hairpin RNA (shRNA) to knock down YY1 expression. Both approaches suppressed H3-K27 trimethylation of the IL2 promoter by western (FIG. 2D; Ezh2 inhibitor) and by ChIP/qPCR (FIG. 2E; YY1 shRNA & Ezh2 inhibitor). Confirming the hypothesized suppressive effect of histone trimethylation, T cells continuously blocked for H3-K27 trimethylation with Ezh2 inhibitor sustained IL2 at high levels throughout, exceeding that of control T cells by a factor of >40 after the $4^{th}$ stimulation (FIG. 2F).

In a separate test using YY1 shRNA (FIG. 2G), T cells underwent two control stimulations, releasing ~1500 pg/ml IL2 after each stimulation, and then on day 4, just prior to a $3^{rd}$ stimulation, were either transduced with shRNA plasmid, control plasmid or untransduced. In contrast to Ezh2 inhibition that was continuous through second stimulation to the entire experiment, YY1 inhibition was applied as a transient system because the delivered plasmid that generates shRNA is not stably retained and expressed in the T cells. IL2 secretion was fully exhausted after the $2^{nd}$ stimulation, now releasing only 35 pg/ml following a $3^{rd}$ stimulation. In contrast, the same twice-stimulated exhausted T cells treated with YY1 shRNA had IL2 levels after the $3^{rd}$ stimulation that were 30-fold higher, in excess of 1000 pg/ml. In a further repeat of the assay, using now the control thrice-stimulated exhausted T cells that released only 35 pg/ml IL2, a $4^{th}$ stimulation was performed. This yielded 15 pg/ml IL2 for control but 350 pg/ml from the same exhausted T cells pretreated with YY1 shRNA. YY1 was effectively suppressed on western blot performed two days after shRNA plasmid exposure (FIG. 2G inset); shorter times were not evaluated.

Figure 15:
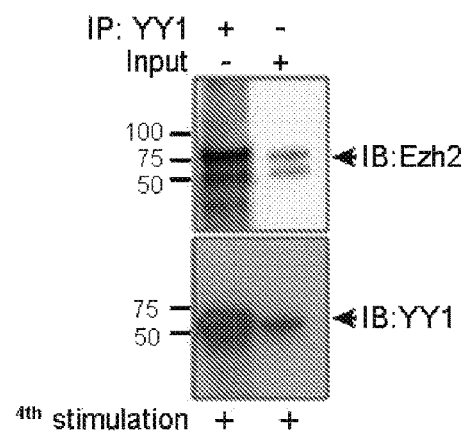
FIG. 15 shows that YY1 interacts with Ezh2 in exhausted T cells.

These YY1 shRNA tests demonstrate the conclusion that IL2 failure can be reversed by interventions rather than prevented. This ability to reverse IL2 exhaustion implies a need for continuously effective histone trimethylation for continued IL2 suppression, marking "exhaustion" itself as an active, energy-requiring process rather than simply a depleted state. The physical association of YY1 and Ezh2 to mediate IL2 suppression was confirmed by co-immunoprecipitation assays using extract from T cells under exhaustion conditions (FIG. 2H and FIG. 15). These results thus support a model of T cell exhaustion in which the IL2 promoter binds YY1, YY1 recruits Ezh2 to the site, Ezh2 trimethylates chromatin and IL2 transcription is repressed (FIG. 2I).

Figure 16:
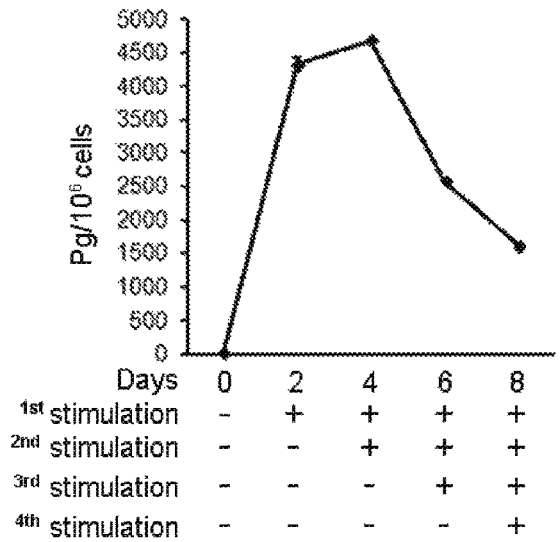
FIG. 16 shows that Ezh2 inhibitor does not protect against IFNγ shutdown.

As a key control in this effort, Ezh2 inhibition did not reverse the IFNγ loss that follows repeated T cell stimulation (FIG. 16). YY1 was previously shown to disrupt transcription of this type I cytokine by a distinct mechanism from what was described for IL2, by competing for AP1 binding via an overlapping YY1 binding site, in which AP1 is a prime activator of IFNγ transcription (Ye et al., 1996 Mol Cell Biol 16, 4744-4753).

YY1 Upregulates Exhaustion Markers

The simultaneous rise of Ezh2 along with PD1, Lag3 and Tim3 indicates coordinate regulation of these genes by YY1 as well. Searching the Transfac database (Biobase), PD1 and Lag3 promoters were found to contain consensus binding sites for YY1 (FIG. 17A, B), whereas Ezh2 and Tim3 lacked such sites.

Figure 3:
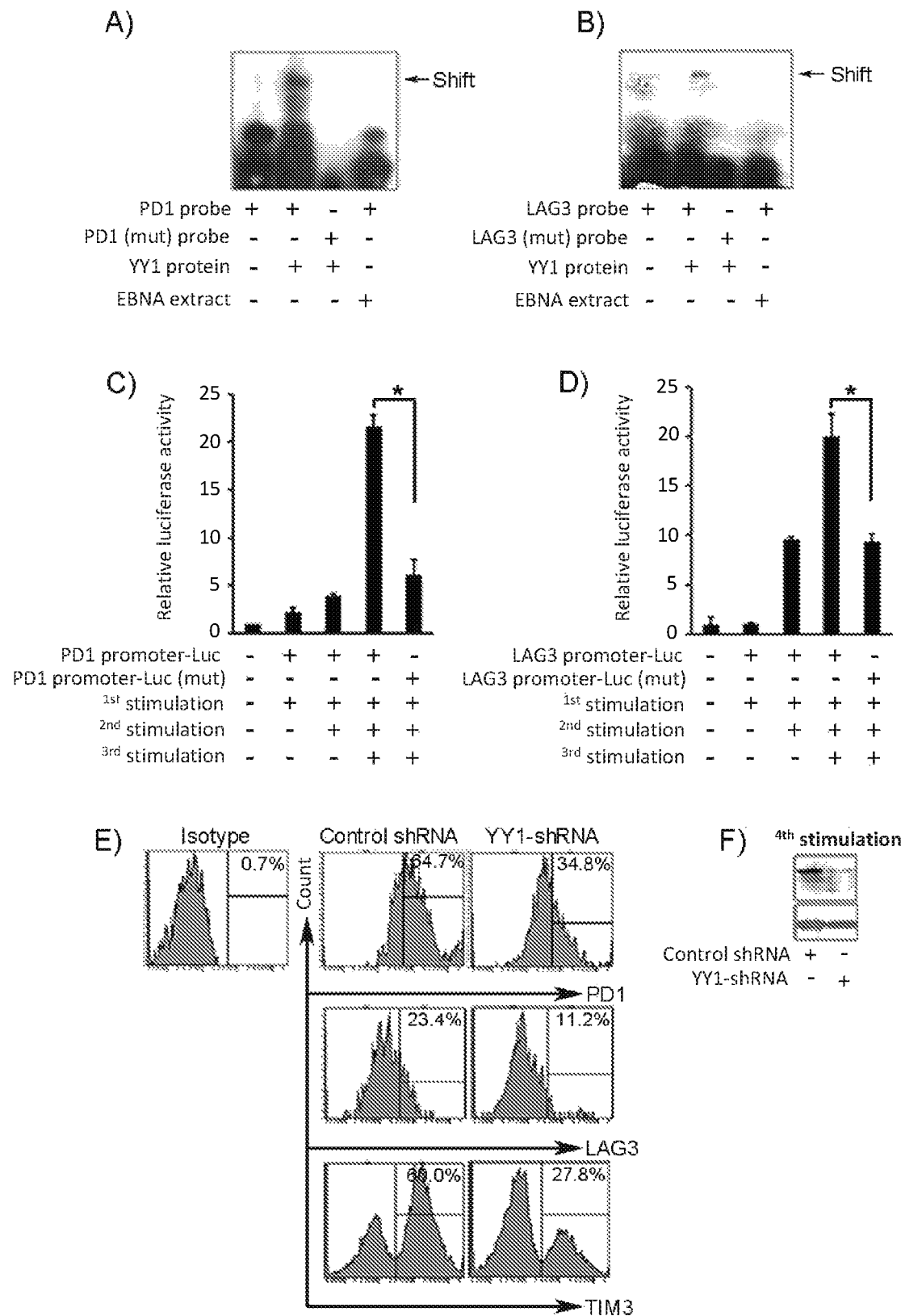
FIG. 3 shows that YY1 upregulates checkpoint receptors in exhaustion. (A-B) Electromobility shift assay (EMSA) shows YY1 binding to PD1 and Lag3 promoters. Recombinant YY1 protein was incubated with PD1 and Lag3 probes containing intact (Lane 2) or mutated YY1 binding sites (Lane 3). Epstein-Barr nuclear antigen (EBNA) extract was control non-specific extract (Lane 4). (C-D) Luciferase reporter assay shows increased activity with PD1 and Lag3 reporter plasmids in re-stimulated CD8 T cells with intact YY1 binding sites and activity loss with YY1 mutated sites. Three replicates per assay; *$p<0.05$. (E) Flow cytometry shows suppression of increase of PD1, Lag3 and Tim3 in CD8 T cells expressing lentiviral YY1-shRNA. (F) YY1 knockdown achieved with YY1 shRNA compared to control after 4 stimulations.

PD1 and Lag3 genes were examined for regulation by YY1. Gel shift assay confirmed that YY1 binds specifically to the consensus sites present in PD1 and Lag3 promoters (FIG. 3A, B). Reporter gene assays showed increased transcription with repeat T cell stimulations that was abrogated by mutation of the YY1 binding sites, confirming that PD1 and Lag3 genes are positively regulated by YY1 (FIG. 3C,D). Finally, knockdown of YY1 in repeatedly stimulated cells markedly reduced PD1 and Lag3, as predicted, but also Tim3 (FIG. 3E, F), indicating that YY1 regulates Tim3 as well but by indirect means. The Tim3 promoter carries a binding site for GATA3 (FIG. 17C), which is known to bind YY1 to enhance transcriptional activity in the absence of a separate YY1 binding site (Hwang et al., 2013 Oncogene 18, 6087-6093), again supporting the centrality of YY1 to broad elements of the exhaustion process. Knockdown of YY1 had no impact on Ezh2 levels, indicating that Ezh2 regulation is through an independent mechanism that parallels rather than depends on YY1.

cJun/ATF2 Upregulates YY1

Figure 4:
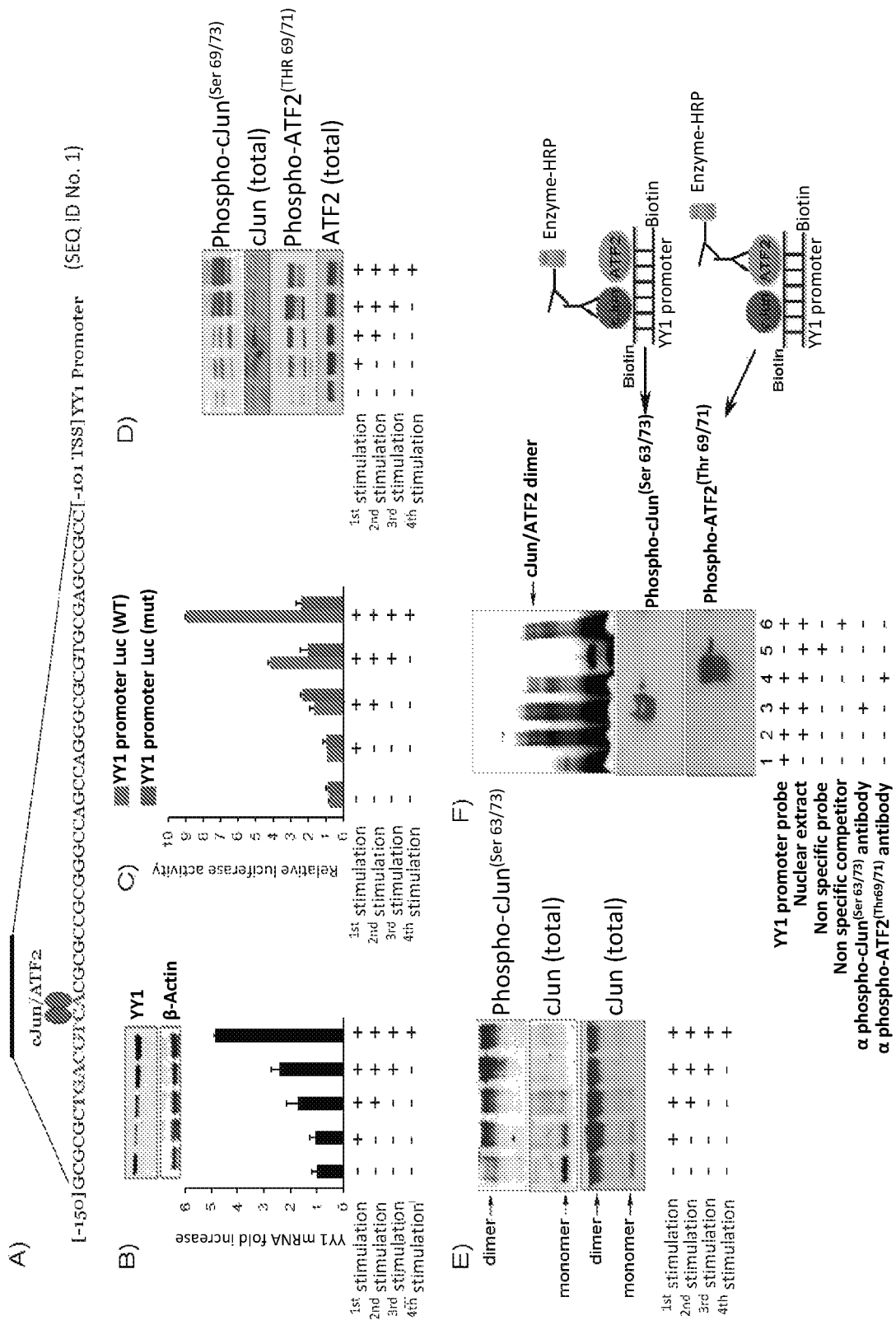
FIG. 4 shows that cJun/ATF2 stimulates YY1 transcription. (A) YY1 promoter sequence shows cAMP response element (CRE) binding site for cJun/ATF2 at −136 relative to transcription start site (TSS). (B) Western blot (upper) and qRT-PCR (lower) shows increase of YY1 protein and mRNA in CD8 T cells with restimulation. Three replicates per assay. (C) Luciferase reporter gene assay of YY1 promoter shows increased activity with re-stimulation and activity loss with mutation of CRE site. (D) Western blot shows increased phospho-cJun and phospho-ATF2 in CD4 T cells after re-stimulation. (E) Native gel analysis shows increased phospho-cJun dimer formation with restimulation and loss of monomer detected by specific antibodies. (F) EMSA confirms binding of phospho-cJun and phospho-ATF2 to site on YY1 promoter. Bottom panel: Western blot developed after species specific secondary antibody to detect primary antibodies bound to probe.

Experiments were next performed to understand the connection between T cell activation and exhaustion, specifically, what precedes YY1 upregulation. Examination of the YY1 promoter revealed an octameric palindrome cyclic AMP-response element (CRE) (TGACGTCA) for binding the cJun/ATF2 transcription factor complex (van Dam and Castellazzi, 2001 Oncogene 20, 2453-2464) (FIG. 4A and FIG. 17D). (FIG. 17E summarizes the relevant TF binding sites in this report). Repeated stimulation yielded increased YY1 mRNA and protein levels (FIG. 4B) as above (FIG. 2A-C). A YY1 reporter assay showed progressively increased activity with repeat T cell stimulation that was abrogated upon mutating the CRE site (FIG. 4C), thus confirming the role of cJun/ATF2 binding.

To stimulate transcription, non-phosphorylated cJun and ATF2 monomers that predominate in resting state undergo conversion to their transcriptionally active phospho-forms (Smeal et al., 1992 Mol Cell Biol 12, 3507-3513) as seen on repeat stimulation in the system (FIG. 4D). Next, phospho-cJun forms either homodimers with itself or heterodimers with phospho-ATF2 (Hayakawa et al., 2004 Mol Cell 16, 521-535). With repeated stimulations in the T cells, the majority of phospho-cJun was confirmed to form dimers on native gels (FIG. 4E). Further, dimer was seen to bind to YY1 probe on gel-shift assay (FIG. 4F, Lanes 2-4) that was confirmed by antibody staining to contain phospho-cJun (Lane 3) and phosph-ATF2 (Lane 4). Taken together, these data confirm that phospho-cJun/ATF2 dimer physically binds to the CRE element to upregulate YY1 expression in chronically stimulated T cells.

p38MAPK/JNK Pathway Phosphorylates cJun/ATF2

Experiments were next performed to define the upstream elements that precede cJun/ATF2 transcription factor phosphorylation and activation. The p38MAPK/JNK2 stress signaling pathway has a complex array of activities that are cell- and context-dependent, initiated in the current context by the combination of TCR/CD3 and CD28 signaling (Davis, 2000 Nature 443, 350-354). Here, it is contemplated that this prominent pathway, upon persistent stimulation, leads to cJun and ATF2 phosphorylation, YY1 promoter activation and ensuing T cell exhaustion (FIG. 5A).

To test the explanatory value of the model (FIG. 5A), lysates from T cells persistently activated in vitro to analyze phospho-p38$\alpha^{(Tyr323)}$ (alternative p38 activation pathway), phospho-p38$\alpha^{(Thr180/Tyr182)}$, phospho-AKT$^{(S473)}$, phospho-JNK2$^{(T183/Tyr185)}$, phospho-MKK4$^{(Ser257/Thr261)}$, phospho-MKK3$^{(Ser189/Thr193)}$, and phospho-ZAP70$^{(Tyr319)}$ were examined. Upon repeated stimulation, these kinases underwent a progressive increase in phosphorylation (FIG. 5B).

To probe the relation of this pathway to YY1 expression, selective inhibitors that block phosphorylation of JNK, p38MAPK and MEK1 (FIG. 18A) were used, with the latter included as a non-pathway control. YY1 luciferase reporter showed high transcriptional activity after four stimulations that were suppressed by inhibitors to p38MAPK or JNK, confirming their roles in YY1 transcription, with no impact from MEK1 inhibitor, confirming that the MEK1 pathway is not involved (FIG. 5C upper). These tests also showed markedly reduced YY1 protein in the same cells (FIG. 5C lower).

These data are consistent with a pathway beginning at the membrane with 2-signal T cell stimulation to p38MAPK/JNK activation to phosphorylation of ATF2/cJun in the cytoplasm with nuclear translocation and then activation of YY1 transcription that in turns directs the exhaustion phenotype that ensues. The total YY1-centered circuit from T cell activation to exhaustion as revealed by these studies is depicted graphically in FIG. 19.

Restimulation Induces Functional Exhaustion

Conventional markers of T cell exhaustion (e.g., checkpoint receptor expression, cytokine loss) are indicators or mediators: the key functional outcome of exhaustion is its adverse impact on killing of pathogenic targets, e.g, tumor or virus-infected cells. The in vitro model successfully reproduces the markers of in vivo-exhausted T cells, but it cannot directly address cytotoxic activities without antigenic targeting. In this section, analysis is extended via a related model that allows antigen selection as well as control of the number of signals involved.

Chimeric antigen receptor (CAR)-modified T cells with one or two signals that enable a direct assay of killing against cells expressing carcinoembryonic antigen (CEA) (FIG. 6A) (Emtage et al., 2008, supra) were incubated the CAR-T cells with an excess of CEA+ tumor cells and the T cells were followed for exhaustion marker responses. There was a progressive increase in PD1 and Lag3, but only with the construct generating 2 signals (FIG. 6B, C), paralleling the results in normal unmodified T cells (FIG. 1C). (All subsequent data pertain solely to signal 1+2 [$2^{nd}$ generation] CAR-T.) As previously determined (Emtage et al., 2008, supra) and as also reproduced in normal unmodified T cells above, there was a high initial secretion of IL2 via signal 1+2 by CAR-T on CEA+ targets that declined with subsequent tumor cell exposures (FIG. 6D). Finally, referencing cytotoxicity as the ultimate functional outcome, killing was robust with the first CAR-T exposure to tumor, but then declined with subsequent exposures, compatible with T cell functional exhaustion (FIG. 6E). The in vitro restimulation model is therefore confirmed by this final functional criterion as replicating in vivo T cell exhaustion responses.

Figure 20:
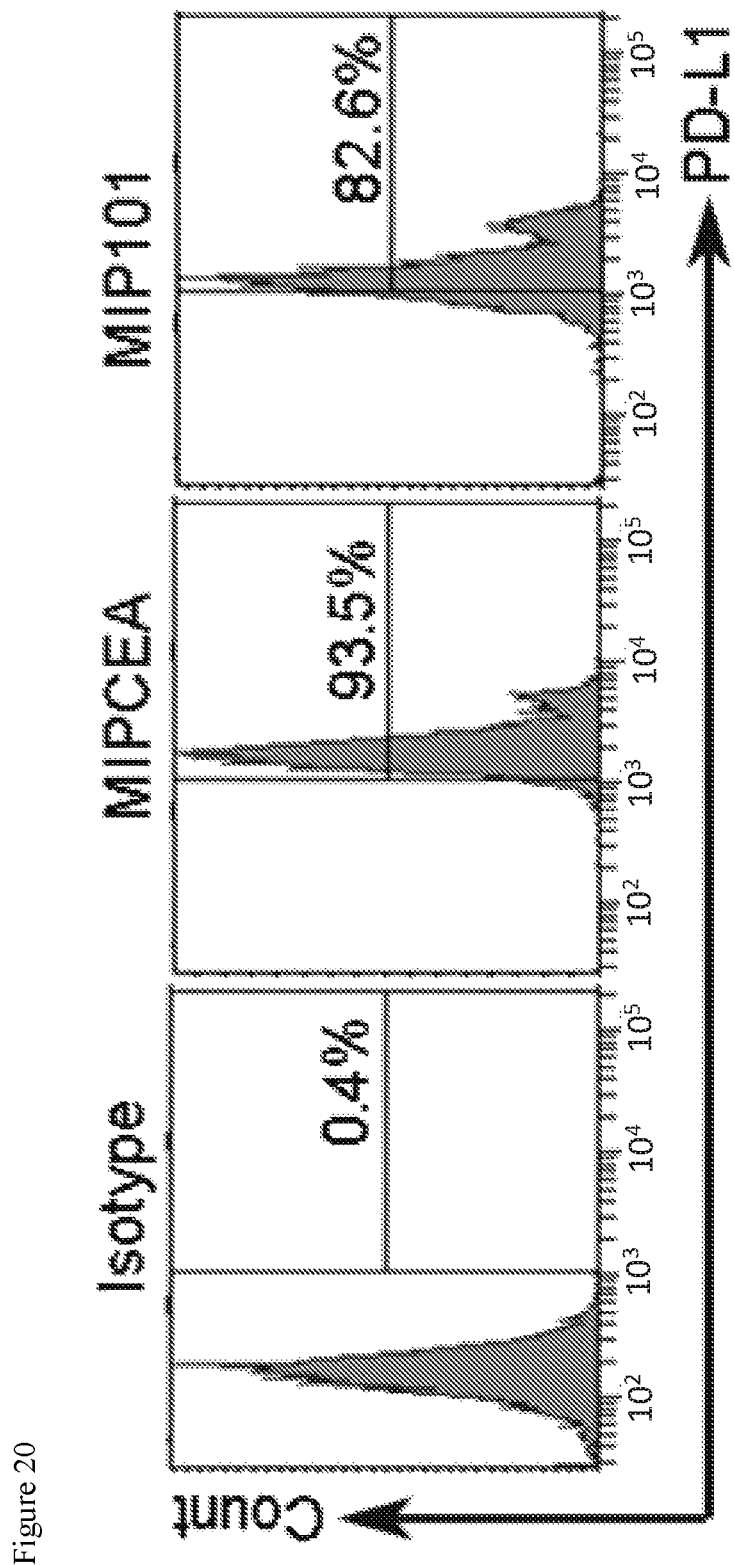
FIG. 20 shows that MIPCEA and MIP101 tumors are positive for PDL1.

To assess selectively the contributions of IL2 failure versus checkpoint receptor action in the functional decline of exhausted T cells, it was investigated if blocking Ezh2 or checkpoint receptor PD1 could restore the cytotoxic potency of the exhausted T cells. Because Ezh2 inhibition appears only to reverse IL2 suppression with no impact on other aspects of the exhaustion phenotype, any activity of the checkpoint receptors to mediate this exhaustion could continue uninterrupted. Specifically, the MIPCEA cell line is strongly PDL1+ (FIG. 20) with the potential to continue to drive exhaustion if the PD1-PDL1 axis were the prime regulator of exhaustion.

CAR-T cells treated with Ezh2 sustained their antigen-specific IL2 production under exhaustion promoting conditions (FIG. 6F). The CAR-T cells in the presence or absence of Ezh2 inhibitor performed robust killing against antigenic targets equally during the first exposure to tumor cells (compare FIG. 6G with FIG. 6E), whereas only Ezh2 inhibitor-treated CAR-T cells maintained efficient killing with each subsequent exposure for a net 5-fold benefit by the $3^{rd}$ co-culture. An anti-IL2 neutralizing antibody applied to the Ezh2 inhibitor group successfully blocked 60-70% of the restored killing activity, confirming that the benefit of Ezh2 inhibitor was from sustained IL2 (FIG. 6G-H).

In other tests, blocking of the PD1-PDL1 axis with anti-PD1 antibody, nivolumab was performed. In line with nivolumab's action to oppose exhaustion in human clinical studies (Rajan et al., 2016), nivolumab partially rescued the loss of T cell cytotoxic potency during repeated exposures of CAR-T cells to tumor, but to a lesser degree than Ezh2 inhibition (30% rescue by nivolumab versus 100% rescue by Ezh2 inhibitor in 3rd co-culture; FIG. 21A-D). This result may indicate that IL2 failure is of even greater importance than PD1-PDL1 signaling to functional suppression under some exhaustion conditions. Nivolumab interrupts the action of PD1 to upregulate phosphotases that inhibit TCR activation (Freeman et al., 2000 J Exp Med 192, 1027-1034) by a non-IL2 dependent mechanism. Nivolumab-treated CAR-T cells experienced the same IL2 loss as control T cells, indicating that restoring IL2 is not part of how nivolumab acts (FIG. 21E).

Ex Vivo Markers of Exhaustion in Cancer and HIV

Figure 7:
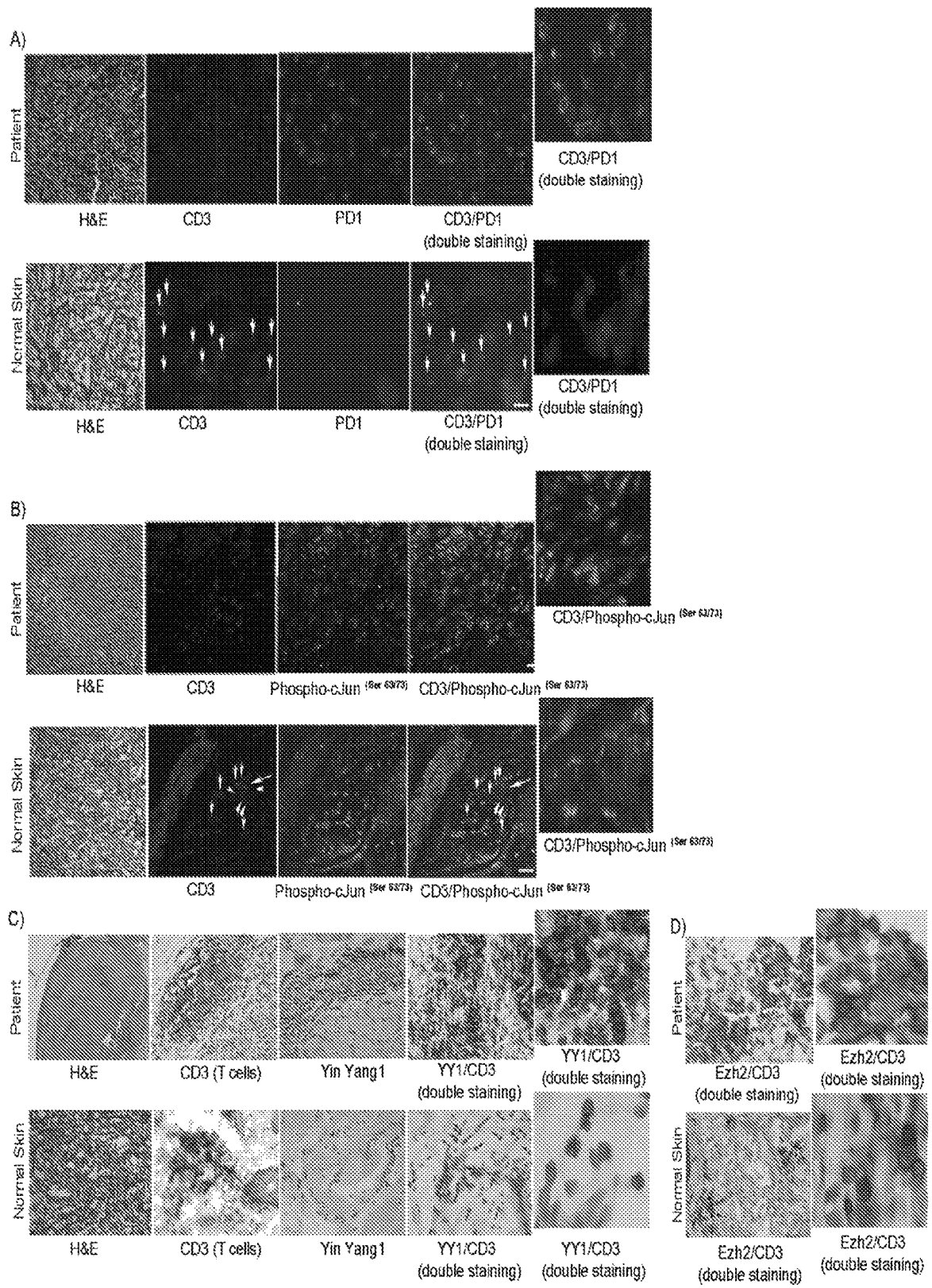
FIG. 7 shows new exhaustion markers confirmed in melanoma TILs. (A-B) Human melanoma sections for Melan-A (MART 1 underwent IF staining, showing most infiltrating T cells are PD1+ (CD3 and PD1 double staining) and activated phospho-cJun$^{(ser63/73)}$ positive (CD3/phospho-cJun$^{(ser63/73)}$ double staining). (C-D) IHC showing expression of YY1 and Ezh2 in TILs, confirmed on double staining. Normal skin T cells were negative for YY1 and Ezh2, bottom panels. Scale bar=20 μm.

T cells reactive to melanoma antigen Melan-A/MART1 commonly infiltrate tumor sites (i.e., tumor-infiltrating lymphocytes, TILs), but are functionally exhausted as evidenced by loss of type I cytokines, expression of genes associated with exhaustion, including PD1, and lack of tumor cell killing (Baitsch et al., 2011, supra). Fifteen human melanoma samples and 10 normal skin biopsies were examined and it was confirmed that the majority of TILs were exhausted per PD1 positivity while normal skin T cells were negative (FIG. 7A). These tissues were then assayed for the features revealed in the in vitro exhaustion system. Staining confirmed elevated phospho-cJun$^{(Ser63/73)}$ protein in the TILs, indicating activation of the p38MAPK/JNK pathway, and a broad YY1 positivity (FIG. 7B, C). YY1-cofactor Ezh2 was also elevated (FIG. 7D). Resident T cells in normal skin were negative for all markers. These in vivo data on exhausted T cells thus replicate and validate the findings derived from the in vitro modeling: activation of p38MAPK/JNK pathway in TILs driving YY1 expression that in turn upregulates PD1 and mediates the diverse other aspects of the exhaustion phenotype (FIG. 19).

Figure 8:
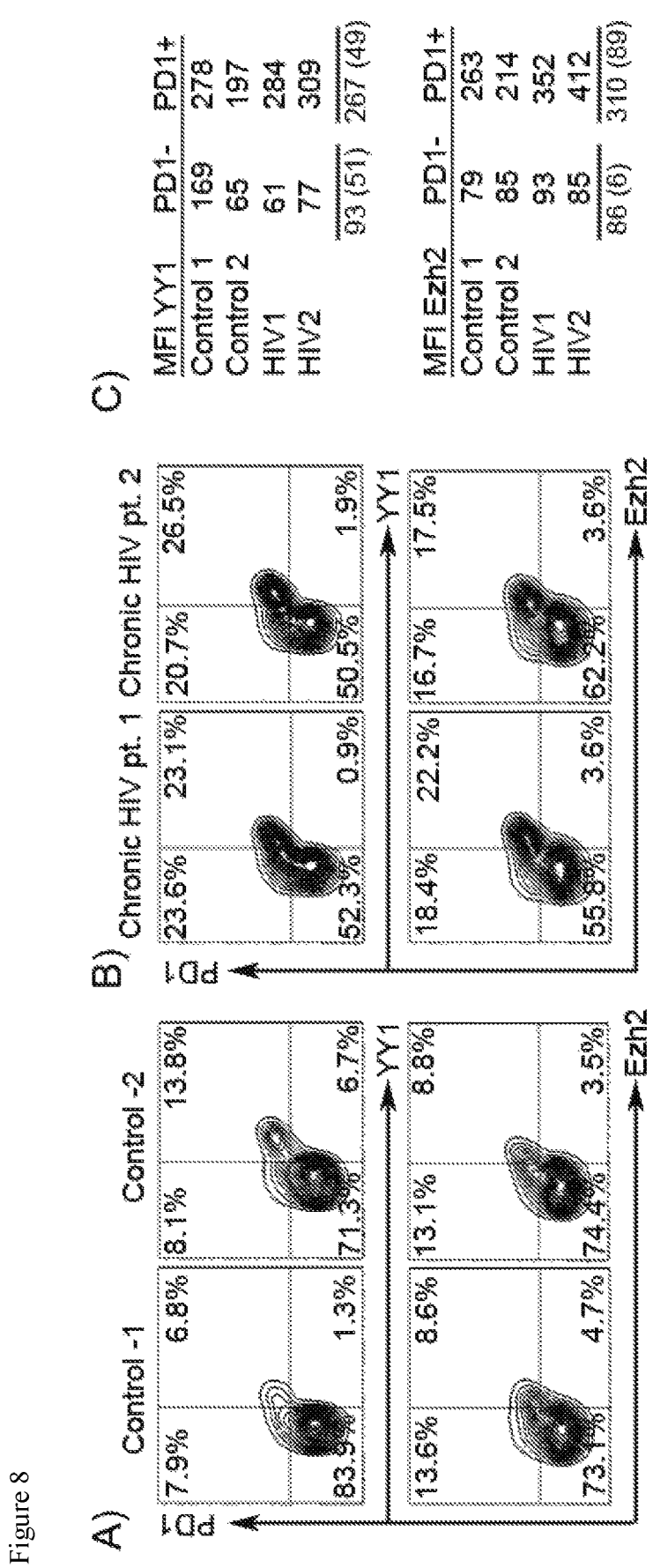
FIG. 8 shows new exhaustion markers confirmed in HIV T cells. CD4 T cells from (A) control subjects and (B) HIV patients were stained and analyzed by flow cytometry for PD1 and YY1 or PD1 and Ezh2. (C) Summary of MFI values for YY1 and Ezh2 in PD1− and PD1+ CD4 T cells.

As a further test of the breadth of the model for exhaustion regulation, T cells from an infectious disease setting were examined. T cell exhaustion was first recognized in infections rather than cancer, specifically in experimental LCMV infections in mice, and later in chronic infections in humans, including HIV (Barber et al., 2006, supra; Wherry, 2011, supra). PD1 expression on CD4 and CD8 T cells in untreated HIV infection has been associated with functional exhaustion, with higher fractions of PD1+ CD4 cells correlating with higher viral load and low CD4 counts (Day et al., 2006 Nature 443, 350-354; Grabmeier-Pfistershammer et al., 2011 J Acquir Immune Defic Syndr 56, 118-124). Further, the PD1+ CD4 T cell subset, which is restrained from activation and proliferation by exhaustion, is favored as a reservoir for latent HIV in patients on antiretroviral therapy (Hatano et al., 2013 J Infect Dis 208, 50-56). CD4 T cells were examined by flow cytometry from ten (n=10) chronically infected untreated HIV patients and an equal number of healthy donors (FIG. 8A, B). These tests confirm that the PD1+ populations are shifted towards YY1 expression and Ezh2 expression for both normal and HIV+ subjects, in parallel to findings with the in vitro exhaustion model and the ex vivo melanoma tests.

In conclusions, the above results demonstrate that 1) Exhaustion is characterized by dysregulation of two axes: upregulation of checkpoint receptors (e.g., PD1, Lag3) and downregulation of type I cytokines (e.g., IL2, IFNg); 2) YY1 controls expression of both the checkpoint receptor and cytokine axes; 3) YY1 is increased in chronically activated T cells via 2-signal stimulation and a signaling cascade culminating in cJun/ATF2 binding to and activating the YY1 promoter; 4) Inhibition of YY1 by siRNA or inhibitors against components of the cascade results in reduced checkpoint receptors and increased cytokine with stored T cell function and resistance to T cell exhaustion; 5) Ezh2 increases in restimulated T cells in parallel to YY1; 6) Ezh2 collaborates with YY1 in suppressing IL2 production in the cytokine axis of exhaustion; 7) Ezh2 inhibitor restores IL2 production, blocking the IL2 part of the cytokine axis of exhaustion; 8) Checkpoint receptor axis blockade with nivolumab partially restores functional killing activity of exhausted specific T cells; 9) Cytokine suppression axis blockade with Ezh2 inhibitor restores functional killing activity of exhausted specific T cells to a greater degree than checkpoint receptor blockade; 10) Ezh2 inhibitor is more effective than checkpoint receptor antibodies in restoring function to exhausted T cells; 11) The combination of Ezh2 inhibitor and checkpoint receptor antibodies, attacking both axes of exhaustion, provides a more complete reversal of exhaustion than either alone; and 12) YY1 inhibition is effective in suppressing both the checkpoint receptor axis and the cytokine repression axis of exhaustion for the most complete reversal of exhaustion, and can be used in conjunction with checkpoint receptor antibody and/or Ezh2 inhibition in specific settings.

EXAMPLE 1

Testing for Exhausted T Cells: YY1, Ezh2 and PD1 Assay Intratumoral T Cells in Cancer Tumor biopsies are assayed through Immunohistochemistry (IHC) or Immunoflourscence (IF) methods to detect exhausted T cells. Exhausted T cells are identified through using PD1/CD3 staining (Baitsch et al, 2009). In some assays, PD1 may be costained for YY1 or Ezh2 to confirm their co-expression. The tumor biopsies are formalin-fixed paraffin tissues or fresh-frozen sections mounted on slides. Methods are described under Experimental Methods. If the exhausted fraction of T cells is greater than 1%, 5%, 10%, 20% or other specified number, the patients are considered suitable for reversing exhaustion by these methods to achieve a beneficial clinical result.

PBMCs in Chronic HIV

HIV patients untreated with high viral load in excess of 20,000 copies/ml or on ART therapy with low viral load have PBMC assayed for exhausted T cells. This is performed by PD1/CD3 staining using flow cytometry methods. In some assays, T cells are stained for PD1 and coexpression of YY1 and Ezh2. In some assays CD8 T cells or CD4 T cells are enriched from the PBMCs of HIV patients and assayed for PD1/YY1/Ezh2. In some assays PBMCs are cyto-spun and mounted on slides for IF and IHC analysis to determine the expression of PD1/YY1/Ezh2. Methods are described under Experimental Methods. If the exhausted fraction of the T cells is greater than 1%, 5%, 10%, 20% or 50% or other specified number, the patients are considered suitable for reversing exhaustion by these methods to achieve a beneficial clinical result.

PBMCs in Chronic HIV Using MHC Class I and II Restricted Epitope Tetramers

HIV patients untreated with high viral load in excess of 20,000 copies/ml or on ART therapy with low viral load have PBMC assayed for exhausted T cells among virus-specific T cells. T cells are assayed through flow cytometry for the CD8 or CD4 T cells expressing PD1 and coexpressing YY1 and Ezh2 using MHC restricted HIV antigen specific tetramers. In some assays tetramer positive CD8 or CD4 T cells are cyto-spun and mounted on slides for IF and IHC analysis to determine the expression of PD1/YY1/Ezh2. Methods are described under Experimental Methods. If the exhausted fraction of virus-specific T cells is greater than 1%, 5%, 10%, 20% or 50% or other specified number, the patients is considered suitable for reversing exhaustion by these methods to achieve a beneficial clinical result.

Intrahepatic T Cells in Chronic HBV

Patients are selected displaying clinical, biochemical, and virological evidence of chronic hepatitis B infection with a viral load ranging from 5000 copies/ml or above. Liver biopsies are be assayed through Immunohistochemistry (IHC) or Immunoflourscence (IF) methods to detect exhausted T cells. Exhausted T cells are identified through using PD1/CD3 staining. In some assays, PD1 is costained for YY1 or Ezh2 to confirm their co-expression. The liver biopsies are formalin-fixed paraffin tissues or fresh-frozen sections mounted on slides. Methods are discussed under Experimental Methods. If the exhausted fraction of T cells is greater than 1%, 5%, 10%, 20% or other specified number, the patients is considered suitable for reversing exhaustion by these methods to achieve a beneficial clinical result.

PBMCs in Chronic HBV

Patients are selected displaying clinical, biochemical, and virological evidence of chronic hepatitis B infection with a viral load ranging from 5000 copies/ml or above. HBV antigen specific CD8 or CD4 T cells and tetramer positive cells expressing PD1 and coexpressing YY1 and Ezh2 is determined through flow cytometry analysis. In some assays, tetramer positive CD8 or CD4 T cells are cyto-spun and mounted on slides for IF and IHC analysis to determine the expression of PD1/YY1/Ezh2. If the exhausted fraction of T cells is greater than 1%, 5%, 10%, 20% or 50% or other specified number, the patients are considered suitable for reversing exhaustion by these methods to achieve a beneficial clinical result.

Preventing and Reversing T-Cell Exhaustion in Disease

EXAMPLE 2

Unmodified Host: Infection

Patients suffering from chronic HIV, HCV, HBV infections are extensively reported to have T cells exhausted (Day et al., 2006; Peng et al., 2008; Porichis and Kaufmann, 2011, 2012; Protzer et al., 2012; Zhang et al., 2007). The viral-antigen specific T cells can be found but such T cells remain dysfunctional exacerbating the progression of infection (Day et al., 2006, supra; Goepfert et al., 2000 J Virol 74, 10249-10255; Klenerman and Hill, 2005 Nat Immunol 6, 873-879).

T cell exhaustion in chronic virus infections is characterized by their poor effector functions including diminished cytolytic functions, IFNγ, beta chemokines and IL2 synthesis. Again, IL2 shutdown in virus specific T cells being the major contributor of T cell exhaustion. Furthermore, exhausted T cells in chronic virus infections express inhibitory receptor molecules such as PD1, CTLA4, Tim3, Lag3, 2B4 and shift their cytokine expression profile to IL10 and TGFβ production (Day et al., 2006, supra; Grosso et al., 2009 J Immunol 182, 6659-6669; Matsuzaki et al., 2010 Proc Natl Acad Sci USA 107, 7875-7880; Wherry, 2011, supra). Accordingly, an antibody mediated blockade of PD1 receptor ligand (PD-L1) alone or in combination with inhibition of IL10 or anti-PD1 alone in animal models restores T antiviral immunity and reduces viral load (Barber et al., 2006, supra; Brooks et al., 2008 Proc Natl Acad Sci USA 105, 20428-20433; Ejrnaes et al., 2006 J Exp Med 203, 2461-2472; Ha et al., 2008a J Exp Med 205, 543-555; Ha et al., 2008b Immunol Rev 223, 317-333).

In some embodiments, patients with chronic viral infections are treated with YY1 or Ezh2 inhibitor drugs as follow: The population of patients suffering from chronic HIV, HCV, HBV infections is sampled to determine PD1 expression on their T cells obtained from peripheral blood mononuclear cells (PBMCs). The procedure of using PD1 as a marker of exhaustion is applied to sample exhausted T cells present in chronic HIV and EBV infections and is, thus, an accepted criteria of exhaustion in chronic viral infections (Day et al., 2006, supra). This analysis is performed in comparison with healthy donors. Alternatively, virus-specific T cells are assayed for PD1 determined by tetramer co-staining. Subsequently, the CD4+ and CD8+ T cells are analyzed for PD1 expression and co-stained for YY1, Ezh2 or cJun expression. This is followed by treatment with YY1 and Ezh2 inhibitors. The YY1 or Ezh2 inhibitor drugs are directly injected or orally administered, e.g., i.p, i.v routes into patients suffering from chronic viral infections such as HIV, HCV, HBV.

Therefore, a major effect of YY1 or Ezh2 inhibitor drugs is expected to be on the virus-specific exhausted T cells that may reverse exhaustion by restoring IL2 production and T cell proliferation and YY1 knockout apart from IL2 rescue is expected to reduce exhaustion markers of PD1, Lag3 and Tim3.

EXAMPLE 3

Unmodified Host: Cancer

Exhausted T cells in reactive tumors have low proliferative capacity, express inhibitory receptor molecules such as PD1, Tim3, Lag3 and lose the ability to produce IL2 cytokine. IL2 plays a pivotal role in clonal expansion of tumor-reactive T cells, in the survival of these cells, and in their activity and persistence in tumor sites (Dudley et al., 2002 Science 298, 850-854; Liao et al., 2013, supra). Therefore, exogenously infused IL2 has demonstrated therapeutic benefit in humans (Rosenberg, 2012 Sci Transl Med 4, 127p5128; Rosenberg et al., 1985a, supra; Rosenberg et al., 1985b, supra). Similarly, blockade of PD1 and Lag3 have shown clinically promising results in reversing exhaustion and eradicating various cancers (Nguyen and Ohashi, 2015, supra; Rosenberg et al., 2011 Cancer Res 17, 4550-4557). Numerous clinical trials are currently underway testing the clinical blockade of PD1 and Lag3 in regaining activity of tumor-specific T cells (Nguyen and Ohashi, 2015, supra). Recently, the FDA has approved nivolumab (PD1 checkpoint inhibitor) for the treatment of metastatic melanoma and advanced non-small cell lung cancer (NSCLC).

In some embodiments, patients with malignant cancers are treated with YY1 or Ezh2 inhibitor drugs as follows: The procedure of treating cancer patients with YY1 or Ezh2 inhibitor drugs is applied to the tumors that are T cell infiltrated and are reported to be exhausted. These include, e.g., ovarian cancer (Preston et al., 2011 Immunotherapy 3, 539-556), melanoma (Boon et al., 2006 Annu Rev Immunol 24, 175-208), non-small lung cancer (Anagnostou and Brahmer, 2015 Clin Cancer Res 21, 976-984), neuroblastoma (Yu et al., 2010 Immunology 129, 474-481), synovial sarcoma (Robbins et al., 2015 Clin Cancer Res 21, 1019-1027). The tumor biopsies obtained from such patients are double stained using immunohistochemistry or immunofluorscence methods. Biopsies are stained for YY1/PD1 or Ezh2/PD1; YY1/CD3 or Ezh2/CD3 to determine that T cells infiltrating into these reactive tumors are exhausted and that such exhausted T cell express YY1 and Ezh2. This procedure is performed in comparison with the T cells infiltrating tumor adjacent normal tissues. Subsequently, the YY1 or Ezh2 inhibitor drugs are directly injected at the site of tumors. A major effect of YY1 or Ezh2 inhibitor drugs is expected to be on the exhausted T cells infiltrating the tumors to help reverse exhaustion by restoring IL2 production and T cell proliferation. YY1 knockout in TILs apart from IL2 rescue is expected to reduce PD1, Lag3 and Tim3 expression.

EXAMPLE 4

Modified Host: Cancer, TILs Treatment

TILs are exhausted in ovarian cancer (Preston et al., 2011, supra), melanoma (Boon et al., 2006, supra), non-small lung cancer (Anagnostou and Brahmer, 2015, supra), neuroblastoma (Yu et al., 2010, supra), synovial sarcoma (Robbins et al., 2015, supra). The exhaustion of TILs in these cancers is identified by the usual criteria of having low proliferative capacity, loss of interleukin 2 (IL2) synthesis, and expression of inhibitory receptor molecules PD1, Tim3 and Lag3

(Fourcade et al., 2010 J Exp Med 207, 2175-2186; Matsuzaki et al., 2010, supra; Sakuishi et al., 2010 J Exp Med 207, 2187-2194).

In some embodiments, cancer patients are treated with TILs modified with YY1 or Ezh2 inactivation as follows: Tumor infiltrating lymphocytes (TILs) are extracted from the tumor biopsies and grown in cultures. A standard protocol to grow TILs in tissue culture conditions is applied. In some embodiments, commercially available tumor dissociation kits (Miltenyi Biotech) are used. Briefly, tumor biopsies are cut into 2-4 mm and incubate with enzyme mix with continuous rotation at 37° C. Next, samples are re-suspended in RPMI 1640 media and applied to a cell strainer, mesh size 70 μm. The cell strainer is washed with additional RPMI 1640 media and centrifuged at 300×g for 7 minutes. The supernatant is aspirated completely. Cells are re-suspended in appropriate buffer for in vitro culture. A portion of the cells is used for flow cytometry analysis to check the TIL recovery and exhaustion phenotype by determining expression of the inhibitory receptor molecules, PD1, Tim3 and Lag3 together with YY1, Ezh2 and cJun expression. In parallel, TILs are expanded in culture, activated and treated with Ezh2 inhibitor or infected with YY1 shRNA lentiviral particles to determine reversal of exhaustion phenotype. The reversal in exhaustion phenotype is expected due to the rescue of IL2 production and reduced PD1, Lag3 and Tim3 expression. Once these in vitro results are confirmed from sample patients, a similar procedure is applied to the melanoma, ovarian cancer, synovial sarcoma, non-Small lung cancer patients. In such patients, TILs are extracted, expanded ex vivo and treated with YY1 and Ezh2 inhibitors and infused back into subjects to generate antitumor responses.

EXAMPLE 5

Modified Host: Infection, CAR-T Treatment

CAR-T cells have been or are developed to target patients with chronic infections that lead to T cell exhaustion: HIV (Sahu et al., 2013 Virology 446, 268-275), HBV (Chisari and Ferrari, 1995 Annu Rev Immunol 13, 29-60), HCV (Jung et al., 1994 Eur J Clin Invest 24, 641-650), JCV (Yang et al., 2007 Int Immunol 19, 1083-1093). These cells are modified by co-transduction or sequential transduction to express RNAi or Rz or other inhibitory RNA to prevent YY1 and/or Ezh2 expression.

For CAR vector with YY1 and/or Ezh2 knockdown, one may use two separate vector systems to express CARs and YY1 or Ezh2 siRNA, shRNA or miRNA to silence YY1 or Ezh2. In some embodiments, a single vector system employing separate promoters, one specific for CAR transcription and the other promoter for YY1 or Ezh2 siRNA, shRNA or miRNA transcription is used.

In another embodiment, the patients have CAR-T expanded and administered without ex vivo treatment or modification to prevent exhaustion. The CAR-T cells are infused and the patient treated with Ezh2 or YY1 inhibitor for days, weeks, months or years as needed to prevent exhaustion and maintain the antiviral effect.

EXAMPLE 6

Modified Host: Cancer, CAR-T Treatment

CAR-T cells have been developed against a wide array of cancer antigens to target prostate (Junghans et al., 2016), liver, pancreatic (Emtage et al., 2008, supra; Katz et al., 2015 Clin Cancer Res 21, 3149-3159; Posey et al., 2016) Immunity 44, 1444-1454), melanoma (Lo et al., 2010, supra), ovarian (Kandalaft et al., 2011 Clin Oncol 29, 925-933; Song et al., 2011 Cancer Res 71, 4617-4627), lung cancer (Morello et al., 2016 Cancer Discov 6, 133-146; Morgan et al., 2010 Mol Ther 18, 843-851). These cells will be modified by co-transduction or sequential transduction to express RNAi or Rz or other inhibitory RNA to prevent YY1 and/or Ezh2 expression. Etc.

For CAR vector with YY1 and/or Ezh2 knockdown, one may use two separate vector systems to express CARs and YY1 or Ezh2 siRNA, shRNA or miRNA to silence YY1 or Ezh2. In some embodiments, a single vector system employing separate promoters, one specific for CAR transcription and the other promoter for YY1 or Ezh2 siRNA, shRNA or miRNA transcription is used. In another embodiment, patients have CAR-T expanded and administered without ex vivo treatment or modification to prevent exhaustion. The CAR-T cells are infused and the patient treated with Ezh2 or YY1 inhibitor for days, weeks, months or years as needed to prevent exhaustion and maintain the antitumor effect.

In these embodiments, it is contemplated that the requirement for IL2 supplementation for optimal TIL cancer therapy may be diminished or completely removed.

EXAMPLE 7

Co-Application with Other Anti-Exhaustion Measures

Anti-YY1 and/or anti-Ezh2 agents described above are administered in combination with interventions against checkpoint receptors or their ligands ("dual treatment"). Dual treatment may allow for a more complete reversal of exhaustion for an improved therapeutic benefit. Tumors shrink from reversal of T cell exhaustion by checkpoint receptor blockade but also by inhibiting suppression of cytokines during exhaustion, thereby restoring cytokine production that is expected to coordinate with checkpoint receptor suppression to restore T cell function and antitumor potency. The same "dual treatment" strategy is applied in settings with chronic infections as outlined above.

In some embodiments, cancer patients who are eligible for treatment with antibodies for checkpoint receptor blockade (e.g., non-small cell lung cancer, transitional cell cancer, melanoma, others) are treated with checkpoint axis antibody (e.g., nivolumab, atezolizumab) and YY1 and/or Ezh2 inhibitor drugs (dual treatment) as follows: The procedure of applying dual treatment in cancer patients follows the methods established for each of the checkpoint axis antibodies for determining eligibility with specific tumor types: some require testing tumor for PDL1 expression and others do not. If data support that reversal of exhaustion with checkpoint receptor antibodies induces tumor responses, this is considered adequate justification to improve the responses with the addition of YY1 and/or Ezh2 inhibitor strategies.

EXAMPLE 8

Knockout of YY1 or Ezh2 in CAR-T Cells to Resist Exhaustion

Exhaustion is reported in several different CAR-T cells (Long et al., 2015). As a result of exhaustion, CARs developed to treat solid tumors have shown only moderate response in clinical trials (Kershaw et al., 2006 Clin Cancer Res 12, 6106-6115; Park et al., 2007 Mol Ther 15, 825-833; Till et al., 2012 Blood 119, 3940-3950; Lamers et al., 2013 Mol Ther 21, 904-912). Knocking out YY1 or Ezh2 is contemplated to have the same effect as RNAi to these genes in disabling either both axes of the exhaustion phenotype (YY1) or solely the cytokine axis (Ezh2).

To prevent exhaustion of CAR T cells, YY1 and Ezh2 is knocked-out using CRISPR/Cas9-mediated gene knockout in CAR-T cells. YY1 and Ezh2 are knocked out in CAR T cells by electroporating Cas9 mRNA and YY1 and Ezh2 guide RNA (gRNA). YY1 and Ezh2 guide RNA (gRNA) are designed to target YY1 and Ezh2 exons. In some assays, cas-9 is Cas9 ribonucleoproteins (RNPs). In some assays gRNA is sgRNA to recognize the YY1 and Ezh2 genomic sequence. In some assays, Cas9 RNP and in vitro transcribed YY1 or Eh2 are preassembled and then electroporated into T cells.

Because the YY1 or Ezh2 knockout CAR-T cells resist exhaustion, they preferentially grow out in the tumors versus the unprotected CAR-T cells, with a selective enrichment and persistence of protected CAR-T for improved anti-tumor activity in patients.

Analogous applications of YY1 or Ezh2 knockout with TILs, transferred-TCR T cells or anti-viral CAR-T cells is also suitable.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:

1. A method of preventing or reversing T-cell exhaustion in a subject, the method comprising:
   a) (i) downregulating or knocking out the gene expression of YY1 or EZH2 in T-cells of the subject; or
   (ii) inhibiting the protein product of the expression of YY1 or EzH2, in said T-cells; and
   (b) optionally administering a checkpoint inhibitor to the subject.

2. The method of claim 1, wherein said downregulating the expression of YY1 or EZH2 or inhibiting the protein product of the expression of YY1 or EZH2 comprises the use of an agent selected from the group consisting of a nucleic acid, a small molecule, a peptide, a vector, and an antibody, wherein optionally said nucleic acid is selected from the group consisting of an siRNA, miRNA, an antisense nucleic acid, and an shRNA.

3. The method of claim 2, wherein the small molecule is an EZH2 inhibitor.

4. The method of claim 3, wherein said small molecule is selected from the group consisting of 3-Deazaneplanocin A (DZNep), EPZ005687, GSK503, GSK343, GSK126, Ell, and CPI-169T.

5. The method of claim 1, wherein said inhibiting is ex vivo, in vivo, or in vitro.

6. The method of claim 1, wherein said T cells are expanded ex vivo prior to, in conjunction with, or after said inhibiting.

7. The method of claim 1, wherein YY1 and/or EZH2 is expressed or overexpressed in said T cells.

8. The method of claim 1, wherein said T cell:
   (a) comprises a chimeric antigen receptor (CAR);
   (b) comprises a transferred T cell receptor (TCR);
   (c) is modified to have YY1 downregulated or inhibited; or
   (d) is modified to have EZH2 downregulated or inhibited.

9. The method of claim 1, wherein said T-cell is a tumor infiltrating lymphocyte.

10. The method of claim 1, wherein said YY1 inhibitor is on a vector that expresses an siRNA, miRNA, shRNA, or antisense nucleic acid to YY1.

11. The method of claim 1, wherein said YY1 inhibitor inhibits the activity of one or more upstream modulators of YY1.

12. The method of claim 11, wherein said upstream modulator of YY1 is selected from the group consisting of AKT, MEKK1, MKK3/6, MKK4/7, p38, JNK, ATF2, and cJUN.

13. The method of claim 1, wherein said subject has cancer or a chronic infectious disease.

14. The method of claim 13, wherein said chronic infectious disease is a chronic viral disease, a disease caused by an intracellular parasitic organism or a disease caused by an intracellular bacterial organism.

15. The method of claim 13, wherein said T-cell is a tumor antigen reactive T-cell, a viral antigen reactive T-cell, an intracellular bacterial organism antigen reactive T-cell or an intracellular parasitic organism antigen reactive T-cell.

16. The method of claim 13, wherein said chronic infectious disease is selected from the group consisting of HIV, HBV, HCV, CMV, EBV, *M. leprae*, or *Leishmania*, and said cancer is selected from the group consisting of melanoma, non-small cell lung cancer, transitional cell carcinoma, classic Hodgkin's lymphoma, and other cancers that are responsive, improve, or are cured by anti-checkpoint receptor therapy or interleukin 2 or other cytokine supplementation therapy.

17. The method of claim 1, wherein the method further comprises administration of a checkpoint inhibitor to the subject.

18. The method of claim 17, wherein the target of the checkpoint inhibitor is PD1, PD-L1, CTLA-4, or LAG3.

19. The method of claim 18, wherein the checkpoint inhibitor is nivolumab or atezolizumab.

20. A method of treating T cell exhaustion in a subject having cancer or chronic infectious disease in a subject, comprising:
  a) identifying said subject as having a cancer-type or infection-type as being associated with T cell exhaustion when i) the type of cancer is melanoma, transitional coil carcinoma, non-smail cell iung cancer, renal cell carcinoma or other cancer associated with I cell exhaustion; ii) the type of infection is HIV or HBV or other infection associated with T cell exhaustion; iii) the type of cancer is non-small cell iung cancer, transitional coli carcinoma, or other cancer that is responsive or improves or is cured by addressing the checkpoint receptor axis of exhaustion with anti-checkpoint receptor therapy; iv) the type of cancer is melanoma or renal cell carcinoma or other cancer that is responsive or improves or is cured by addressing the cytokine axis of exhaustion with interleukin 2 or other cytokine supplementation therapy; v) the type of infection is HIV or HBV or other infection that is responsive or improves or is cured by addressing the checkpoint receptor axis of exhaustion with anti-checkpoint receptor therapy; or vi) the type of infection HIV or HBV or other infection that is responsive or improves or is cured by addressing the cytokine axis of exhaustion with interleukin 2 or other cytokine supplementation therapy; and
  b) administering an agent that inhibits T cell exhaustion by inhibiting WI expression or activity and/or an agent that inhibits EZH2 expression or activity to said subject.

21. The method of claim 1, wherein the subject has melanoma.

22. The method of claim 1, wherein the subject has non-small cell lung cancer.

* * * * *

UNITED STATES PATENT AND TRADEMARK OFFICE
CERTIFICATE OF CORRECTION

PATENT NO. : 11,624,068 B2
APPLICATION NO. : 16/317446
DATED : April 11, 2023
INVENTOR(S) : Richard P. Junghans et al.

It is certified that error appears in the above-identified patent and that said Letters Patent is hereby corrected as shown below:

In the Claims

Column 51, Claim 1, Line 51, replace "a)" with --(a)--;
      Line 54, replace "EzH2" with --EZH2--.

Column 52, Claim 4, Line 50, replace "E11" with --EI1--.

Column 54, Claim 20, Line 7, replace "coil carcinoma, non-smail cell iung" with --cell carcinoma, non-small cell lung--;
      Line 8, replace "I cell" with --T cell--;
      Line 11, replace "iung" with --lung--;
      Line 12, replace "coli" with --cell--;
      Line 23, replace "infection HIV" with --infection is HIV--;
      Line 29, replace "WI" with --YYI--.

Signed and Sealed this
Fifteenth Day of August, 2023

Katherine Kelly Vidal
*Director of the United States Patent and Trademark Office*